US011944613B2

United States Patent
Sisignano et al.

(10) Patent No.: US 11,944,613 B2
(45) Date of Patent: Apr. 2, 2024

(54) CYP2J2 ANTAGONISTS IN THE TREATMENT OF PAIN

(71) Applicant: FRAUNHOFER-GESELLSCHAFT ZUR FÖRDERUNG DER ANGEWANDTEN FORSCHUNG E.V., Munich (DE)

(72) Inventors: Marco Sisignano, Frankfurt (DE); Christian Brenneis, Kleinostheim (DE); Klaus Scholich, Steinbach (DE); Gerd Geisslinger, Bad Soden (DE); Sebastian Zinn, Frankfurt (DE); Michael John Parnham, Bad Soden (DE)

(73) Assignee: FRAUNHOFER-GESELLSCHAFT ZUR FÖRDERUNG DER ANGEWANDTEN FORSCHUNG E.V., Munich (DE)

( * ) Notice: Subject to any disclaimer, the term of this patent is extended or adjusted under 35 U.S.C. 154(b) by 0 days.

(21) Appl. No.: 16/594,790

(22) Filed: Oct. 7, 2019

(65) Prior Publication Data
US 2020/0101055 A1 Apr. 2, 2020

Related U.S. Application Data

(63) Continuation of application No. 15/503,643, filed as application No. PCT/EP2015/068767 on Aug. 14, 2015, now abandoned.

(30) Foreign Application Priority Data

Aug. 14, 2014 (EP) ..................................... 14181086
Sep. 26, 2014 (EP) ..................................... 14186624

(51) Int. Cl.
A61K 31/445 (2006.01)
A61K 31/138 (2006.01)
(Continued)

(52) U.S. Cl.
CPC .......... *A61K 31/445* (2013.01); *A61K 31/138* (2013.01); *A61K 31/198* (2013.01); *A61K 31/216* (2013.01); *A61K 31/4184* (2013.01); *A61K 31/437* (2013.01); *A61K 31/4545* (2013.01); *A61K 31/495* (2013.01); *A61K 31/496* (2013.01); *A61K 31/498* (2013.01); *A61K 31/517* (2013.01);
(Continued)

(58) Field of Classification Search
CPC ............... A61K 31/138; A61K 31/198; A61K 31/216; A61K 31/4184; A61K 31/437; A61K 31/445; A61K 31/4545; A61K 31/495; A61K 31/496; A61K 31/498; A61K 31/517; A61K 31/558; A61K 31/565; A61K 31/567; A61K 31/573; A61K 31/58; A61K 45/06; A61P 11/02; A61P 13/08; A61P 13/10; A61P 15/00; A61P 17/00; A61P 17/04; A61P 17/06; A61P 19/02; A61P 1/02; A61P 25/00; A61P 25/02; A61P 25/04; A61P 27/16; A61P 29/00; A61P 29/02; A61P 31/18; A61P 35/00; A61P 43/00
USPC ........................................................ 514/172
See application file for complete search history.

(56) References Cited

U.S. PATENT DOCUMENTS 4,783,465 A 11/1988 Sunshine et al.
8,618,286 B2 * 12/2013 Ramnauth ............... A61P 25/06
544/51
(Continued)

FOREIGN PATENT DOCUMENTS

CN 1479628 3/2004
CN 101219142 7/2008
(Continued)

OTHER PUBLICATIONS

Chen et al. (Neuroscience, vol. 193, Oct. 13, 2011, pp. 440-451, Proteinase-activated receptor 2 sensitizes transient receptor potential vanilloid 1, transient receptor potential vanilloid 4, and transient receptor potential ankyrin 1 in paclitaxel-induced neuropathic pain).*
Jaggi et al. (European Journal of Pharmacology, vol. 667, Issues 1-3, Sep. 30, 2011, pp. 215-221).*
Gore et al., "Selecting an Appropriate Medication for Treating Neuropathic Pain in Patients with Diabetes: A Study Using the U.K. and Germany Mediplus Databases", Pain Practice, vol. 8, No. 4, Jul. 1, 2008 (Jul. 1, 2008), pp. 253-262.
(Continued)

Primary Examiner — Shirley V Gembeh
(74) Attorney, Agent, or Firm — Merchant & Gould P.C.

(57) ABSTRACT

The present invention pertains to novel treatments of neuropathic pain; in particular chemotherapy induced peripheral neuropathic pain (CIPNP). The invention provides antagonists cytochrome P450 epoxygenases (CYP), and more specifically antagonists of CYP2J2, as therapeutics for use in the treatment of neuropathic pain such as CIPNP. CYP2J2 antagonists were identified to alleviate CIPNP in-vivo, and therefore are provided additionally in combination with chemotherapeutics for the treatment of diseases such as cancer or other proliferative disorders. The CYP2J2 antagonists reduce chemotherapeutic induced pain and therefore allow for a higher dosing of the chemotherapeutic during cancer treatment. In addition the invention relates to the use of CYP2J2 agonists, or metabolites of CYP2J2, for sensitizing TRPV1. In this context the invention proposes to use combinations of CYP2J2 agonist or metabolites and transient receptor potential vanilloid 1 (TRPV1) agonists to treat disorders that respond to TRPV1 agonists, such as neuropathic pain.

Figure 1:
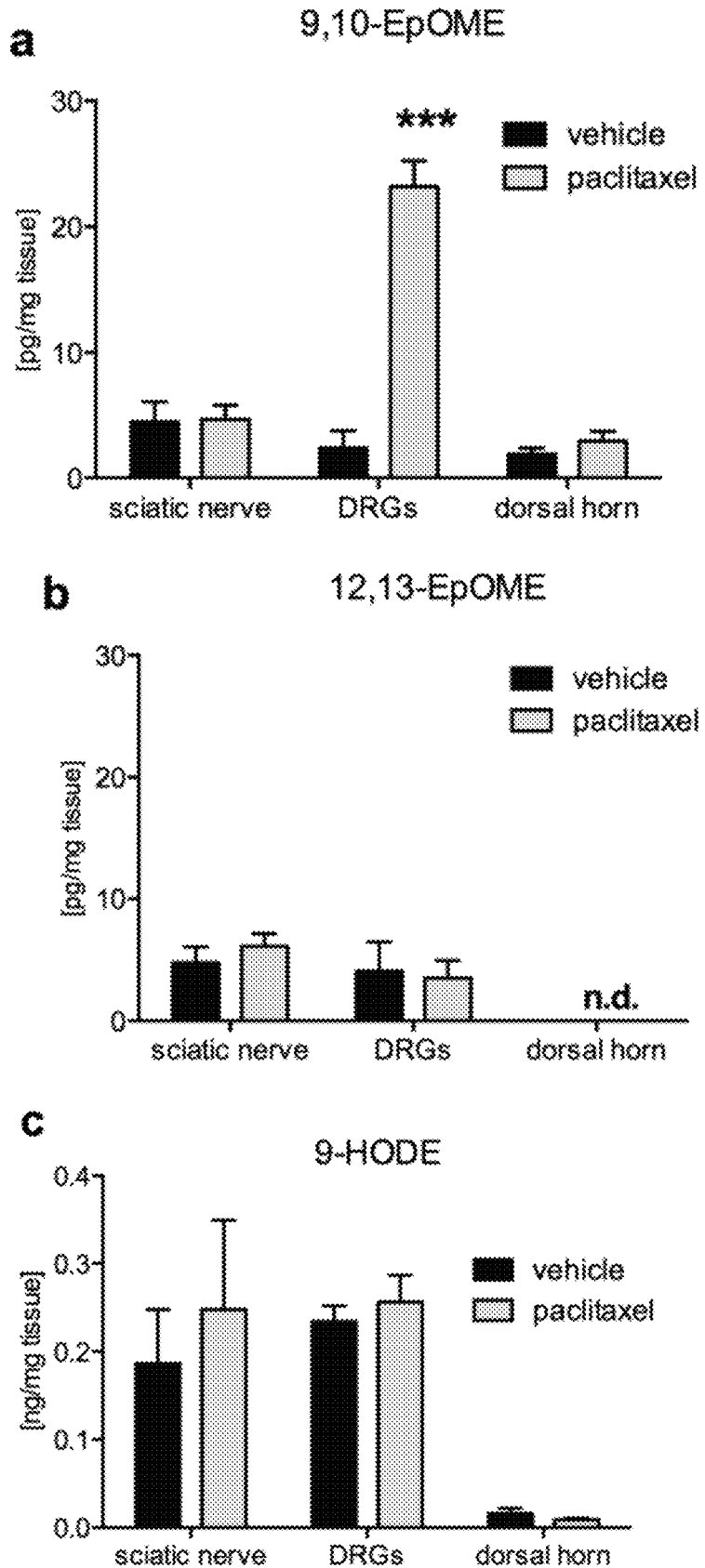
Figure 1:
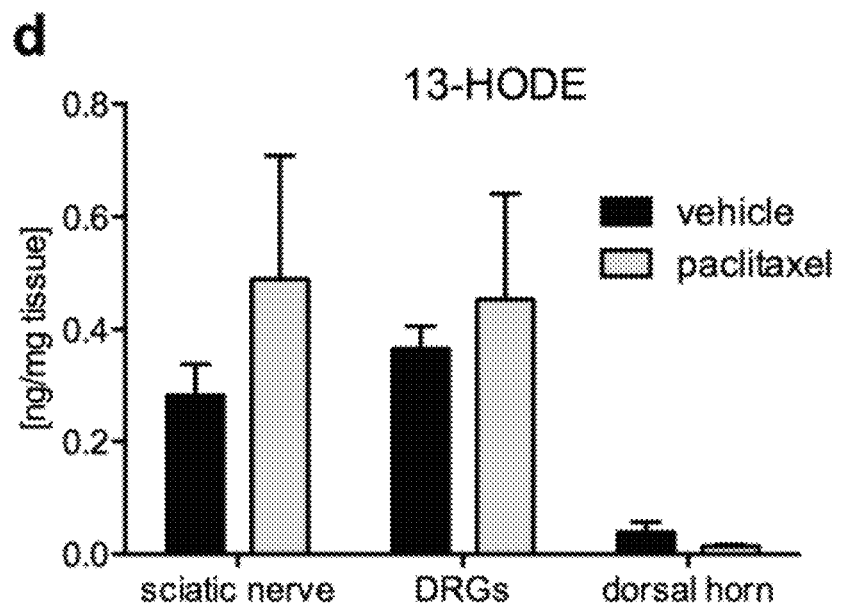
Figure 1:
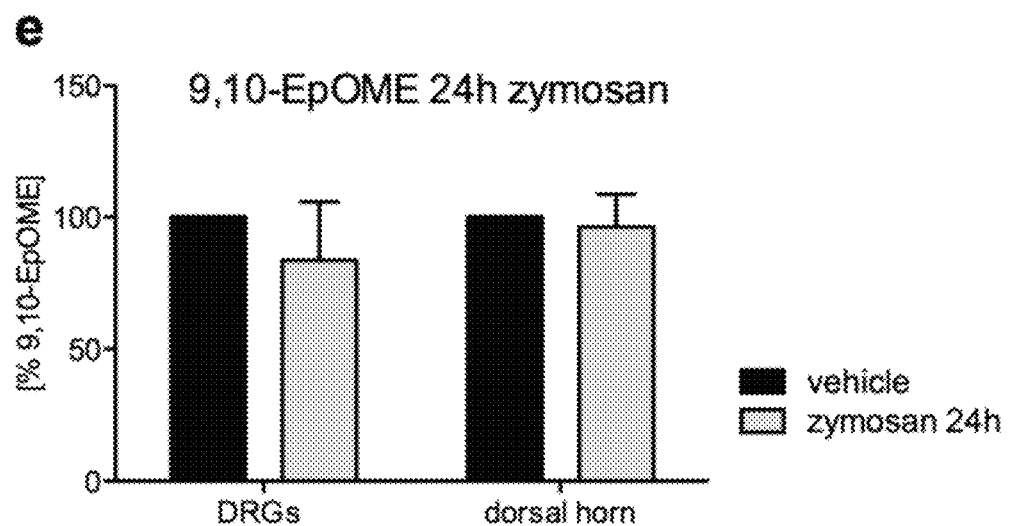

6 Claims, 15 Drawing Sheets
Specification includes a Sequence Listing.

(51) Int. Cl.

| | |
|---|---|
| A61K 31/198 | (2006.01) |
| A61K 31/216 | (2006.01) |
| A61K 31/4184 | (2006.01) |
| A61K 31/437 | (2006.01) |
| A61K 31/4545 | (2006.01) |
| A61K 31/495 | (2006.01) |
| A61K 31/496 | (2006.01) |
| A61K 31/498 | (2006.01) |
| A61K 31/517 | (2006.01) |
| A61K 31/558 | (2006.01) |
| A61K 31/565 | (2006.01) |
| A61K 31/567 | (2006.01) |
| A61K 31/573 | (2006.01) |
| A61K 31/58 | (2006.01) |
| A61K 45/06 | (2006.01) |

(52) U.S. Cl.
CPC .......... *A61K 31/558* (2013.01); *A61K 31/565* (2013.01); *A61K 31/567* (2013.01); *A61K 31/573* (2013.01); *A61K 31/58* (2013.01); *A61K 45/06* (2013.01)

(56) References Cited

U.S. PATENT DOCUMENTS

| 8,809,358 B2 | 8/2014 | Michaelis | |
|---|---|---|---|
| 2009/0069358 A1 | 3/2009 | Michaelis | |
| 2011/0052723 A1* | 3/2011 | Baeyens-Cabrera | .. A61K 31/46 |
| | | | 514/252.12 |
| 2011/0311483 A1* | 12/2011 | Jia | ........................ A61K 31/454 |
| | | | 514/412 |

FOREIGN PATENT DOCUMENTS

| EP | 1944041 | 7/2008 |
|---|---|---|
| WO | 97/07793 A1 | 3/1997 |
| WO | 2010/062900 | 6/2010 |
| WO | 2015/061658 | 4/2015 |

OTHER PUBLICATIONS

Chen et al. "Selective Inhibitors of CYP2J2 Related to Terfenadine Exhibit Strong Activity against Human Cancers in Vitro and in Vivo", Journal of Pharmacology and Experimental Therapeutics, vol. 329, No. 3, Mar. 16, 2009, pp. 908-918.

Naderi et al., "Estradiol attenuates spinal cord injury-related central pain by decreasing glutamate levels in thalmic VPL nucleus in male rats", Metabolic Brain Disease, vol. 29, No. 3, May 31, 2014. pp. 763-770.

Inchiosa, "Phenoxybenzamine in Complex Regional Pain Syndrome: Potential Role and Novel Mechanisms", Anesthesiology Research and Practice, vol. 12, No. 1, Jan. 1, 2013, 7 pages.

Jaggi et al., "Exploring the potential of telmisartan in chronic constriction injury-induced neuropathic pain in rats", European Journal of Pharmacology, Elsevier Science, NL, vol. 667, No. 1, Jun. 14, 2011, pp. 215-221.

Oliveira et al., "Antinociceptive and antiedematogenic activites of fenofibrate, an agonist of PPAR alpha, and bioglitazone, an agonist of PPAR gamma", European Journal of Pharmacologym Elsevier Science, NL, vol. 561, No. 1-3, Mar. 22, 2007, pp. 194-201.

Park, "Chemotherapy induced peripheral neuropathic pain", Korean Journal of Anesthesiology, vol. 67, No. 1, Jan. 1, 2014, 4 pages.

International Search Report and Written Opinion, International Patent Application No. PCT/EP2015/068767, dated Aug. 1, 2016 (25 pages).

Okubo et al., "Inhibition of T-type calcium channels and hydrogen sulfide-forming enzyme reverses paclitaxel-evoked neuropathic hyperalgesia in rates", Neuroscience, vol. 188, Aug. 1, 2011, pp. 148-156.

Office Action; Chinese Patent Application No. 201580042878.4; dated May 17, 2019 (11 pages).

Office Action, Japanese Patent Application No. 2017-503107, dated Jun. 20, 2019, with English translation (14 pages).

Naderi et al., "Estradiol attenuates spinal cord injury-related central pain by decreasing glutamate levels in thalamic VPL nucleus in male rats", Metabolic Brain Disease, vol. 29, No. 3, pp. 763-770 (2014).

Inchiosa Jr., "Phenoxybenzamine in Complex Regional Pain Syndrome: Potential Role and Novel Mechanisms", Anesthesiology Research and Practice, vol. 2013, Article ID 978615, pp. 1-7 (2013).

Jaggi et al., "Exploring the potential of telmisartan in chronic constriction injury-induced neuropathic pain in rats", vol. 667, pp. 215-221, Jul. 11, 2011.

Oliveira et al., "Antinociceptive and antiedematogenic activities of fenofibrate, an agonist of PPAR alpha, and bioglitazone, an agonist of PPAR gamma", European Journal of Pharmacology, vol. 561, pp. 194-201.

Chen et al., "Selective Inhibitors of CYP2J2 Related to Terfenadine Exhibit Strong Activity against Human Cancers in Vitro and in Vivo", Journal of Pharmacology and Experimental Therapeutics, 2009, vol. 329, vol. 329, No. 3, pp. 908-918 (2009).

Cali, "Luminogenic cytochrome P450 assays", Expert Opinion on Drug Metabolism & Toxicology, vol. 2, No. 4, pp. 629-637 (2006).

* cited by examiner a b

CYP2J2 ANTAGONISTS IN THE TREATMENT OF PAIN

FIELD OF THE INVENTION

The present invention pertains to novel treatments of neuropathic pain; in particular chemotherapy induced peripheral neuropathic pain (CIPNP). The invention provides antagonists cytochrome P450 epoxygenases (CYP), and more specifically antagonists of CYP2J2, as therapeutics for use in the treatment of neuropathic pain such as CIPNP. CYP2J2 antagonists were identified to alleviate CIPNP in-vivo, and therefore are provided additionally in combination with chemotherapeutics for the treatment of diseases such as cancer or other proliferative disorders. The CYP2J2 antagonists reduce chemotherapeutic induced pain and therefore allow for a higher and better dosing of the chemotherapeutic during cancer treatment. In addition the invention relates to the use of CYP2J2 agonists, or metabolites of CYP2J2, for sensitizing TRPV1. In this context the invention proposes to use combinations of CYP2J2 agonist or metabolites and transient receptor potential vanilloid 1 (TRPV1) agonists to treat disorders that respond to TRPV1 agonists, such as neuropathic pain.

DESCRIPTION

Neuropathic pain is a persistent or chronic pain syndrome that can result from damage to the nervous system, the peripheral nerves, the dorsal root ganglion, dorsal root, or to the central nervous system. Neuropathic pain syndromes include allodynia, various neuralgias such as post herpetic neuralgia and trigeminal neuralgia, phantom pain, and complex regional pain syndromes, such as reflex sympathetic dystrophy and causalgia. Causalgia is often characterized by spontaneous burning pain combined with hyperalgesia and allodynia. Tragically there is no existing method for adequately, predictably and specifically treating established neuropathic pain as present treatment methods for neuropathic pain consists of merely trying to help the patient cope through psychological or occupational therapy, rather than by reducing or eliminating the pain experienced. Treatment of neuropathic or chronic pain is a challenge for physicians and patients since there are no medications that specifically target the condition, and since the medications presently used result in only little relief and are based on their efficacy in acute pain conditions or on their efficacy on relieving secondary effects like anxiety and depression. Incidence of chronic pain is increasing in society and its burden on society is huge in both health care and lost productivity. Currently there are no scientifically validated therapies for relieving chronic pain. As a result, the health community targets 'pain management' where multi-modal therapies are used concurrently with the hope of providing some improvement in quality of life. Thus, there is an urgent need for drugs that can relieve chronic pain.

Chemotherapy induced peripheral neuropathic pain (CIPNP) is a severe dose limiting side effect of cytostatics, such as taxanes, platinum derivates, vinca alkaloids and others. The symptoms usually start with tingling and can lead to burning, stabbing and aching pain as well as cold and mechanical allodynia. Due to CIPNP some patients stop anticancer therapy with cytostatics too early, resulting in a higher risk of tumor progression. Unfortunately many promising substances, that are already approved for the treatment of different kinds of neuropathic pain, such as gabapentin oramitriptyline seem to have little or no analgesic effect in monotherapy of CIPNP. Understanding the cellular and molecular mechanisms is necessary to treat or even prevent CIPNP and may improve the general success rate of cytostatic therapy.

Recent studies identified members of the transient receptor potential-family of ion channels (TRPV1, TRPA1 and TRPV4) as contributors to both mechanical and cold allodynia during oxaliplatin and paclitaxel-induced neuropathy. Activation or sensitization of TRPV1 and TRPA1 can lead to enhanced release of CGRP and substance P both of which can cause neurogenic inflammation and recruitment of T-cells.

However, it remains unclear which endogenous mediators are involved in cytostatic-dependent activation or sensitization of TRP-channels, as neither of the cytostatics can directly activate TRP-channels. Interestingly, both paclitaxel and oxaliplatin are inducers of CYP-epogenases (paclitaxel: CYP2C8, CYP2C9, oxaliplatin: CYP2E1, CYP1B1). Cytochrome P450 (CYP)-epoxygenases can metabolize ω-6 fatty acids, such as arachidonic acid (AA) and linoleic acid (LA) generating either lipid epoxides such as EETs (epoxyeicosatrienoid acids) or ω-hydroxides such as 20-HETE.

The metabolism of arachidonic acid by cytochrome P450 monoxygenases leads to the formation of various biologically active eicosanoids. Three types of oxidative reactions are known to occur. First, olefin epoxidation (catalyzed by epoxygenases) gives rise to the epoxyeicosatrienoic acids (EETs). Four important EET regioisomers are [5,6]-EET, [8,9]-EET, [11,12]-EET, and [14,15]-EET. The EETs are hydrolyzed by epoxide hydrolases to form the corresponding dihydroxyeicosatrienoic acids (DHETs). Second, omega terminal oxidation leads to the formation of omega terminal hydroxyeicosatetraenoic acids (HETEs). Third, allylic oxidation leads to the formation of midchain HETEs.

Several cytochrome P450 epoxygenases have been identified, including members of the CYP1A, CYP2B, CYP2C, CYP2E, and CYP2J subfamilies. Attention has recently been focused on proteins of the CYP2J subfamily. One particular isoform, CYP2J2, is highly expressed in human cardiac myocytes, where arachidonic acid is metabolized to produce EETs. CYP2J2 proteins are also found in epithelial cells in the airway and in the gut. In contrast to the other P450 enzymes, CYP2J2 proteins are distributed uniformly along the length of the gut, in epithelial and non-epithelial cells. High levels of the CYP2J2 proteins are found in cells of the autonomic ganglia, epithelial cells, and intestinal smooth muscle cells. Several CYP2J homologues have been identified in animals including rat CYP2J3, rat CYP2J4, mouse CYP2J5 and mouse CYP2J6.

Capsaicin is a highly selective agonist for transient receptor potential vanilloid 1 receptor (TRPV1; formerly known as vanilloid receptor 1 (VR1)), a ligand-gated, non-selective cation channel preferentially expressed on small-diameter sensory neurons, especially those C-fibers which specialize in the detection of painful or noxious sensations. TRPV1 responds to noxious stimuli including capsaicin, heat, and extracellular acidification, and will integrate simultaneous exposures to these stimuli. The initial effect of the activation of TRPV1-expressing (capsaicin-sensitive) nociceptors are burning sensations, hyperalgesia, allodynia, and erythema. However, after prolonged exposure to low-concentration capsaicin or single exposures to high-concentration capsaicin or other TRPV1 agonist, the small-diameter sensory axons become less sensitive to a variety of stimuli, including capsaicin or thermal stimuli. This prolonged exposure is also characterized by reduced pain responses. These later-stage effects of capsaicin are frequently referred to as "desensitization" and are the rationale for the development of local capsaicin formulations for the treatment of various pain syndromes and other conditions.

Therefore capsaicin, capsaicinoids and TRPV1 agonists may be useful for amelioration of a plurality of diseases. For example, they may be used to treat neuropathic pain (including pain associated with diabetic neuropathy, postherpetic neuralgia, HIV/AIDS, traumatic injury, complex regional pain syndrome, trigeminal neuralgia, erythromelalgia and phantom pain), pain produced by mixed nociceptive and/or neuropathic mixed etiologies (e.g., cancer), osteoarthritis, fibromyalgia, lower back pain, inflammatory hyperalgesia, vulvar vestibulitis or vulvodynia, sinus polyps interstitial cystitis, neurogenic or overactive bladder, prostatic hyperplasia, rhinitis, surgery, trauma, rectal hypersensitivity, burning mouth syndrome, oral mucositis, herpes (or other viral infections), prostatic hypertrophy, dermatitis, pruritis, itch, tinnitus, psoriasis, warts, cancers (especially skin cancers), headaches, and wrinkles.

Hence, until this day there is no specific therapy for neuropathic pain available, in particular chemotherapy-induced peripheral neuropathic pain (CIPNP), which restricts the maximal dosing of chemotherapeutic agents during cancer treatment and causes severe impairment of life-quality of patients undergoing chemotherapy. The object of the present invention is therefore to provide a novel treatment option to tackle neuropathic pain, specifically CIPNP.

The above problem is solved in a first aspect by a cytochrome P450 epoxygenase (CYP)-antagonist for use in the prevention or treatment of pain in a subject. In some embodiments of the invention the CYP-antagonist is selected from the group consisting of a CYP1A-, CYP2B-, CYP2C-, CYP2E-, and preferably a CYP2J-antagonist. Most preferably the CYP-antagonist is an antagonist of a mammalian homologue of CYP2J2 (CYP2J2-antagonist), preferably human CYP2J2, such as telmisartan, aripiprazole or most preferably terfenadine.

Encompassed by the present invention is the use of any CYP2J2 antagonist, preferably a selective CYP2J2 antagonist. The term "selective CYP2J2 antagonist" pertains to antagonists of CYP2J2 that selectively inhibit activity, function or expression of CYP2J2 but not of other related enzymes such as for example CYP3A molecules. In order to identify whether a candidate antagonist is a CYP2J2 antagonist, a luminogenic cytochrome P450 glow assay can be employed. CYP proteins catalyse the formation of arachidonic acid metabolites. Luminogenic CYP assays use prosubstrates for the light-generating reaction of luciferase. CYPs convert the prosubstrates to luciferin or a luciferin ester, which produces light in a second reaction with a luciferase reaction mix called Luciferin Detection Reagent (LDR). The amount of light produced in the second reaction is proportional to CYP activity.

In order to test selectivity of a candidate CY2J2 antagonist, luminogenic CYP assays specific for other CYP enzymes such as CYP3A4 can be employed. Comparing the inhibitory activity of a candidate antagonist against CYP2J2 with the inhibitory activity of the same antagonist against another CYP protein such as CYP3A4, therefore provides information about the selectivity of the candidate antagonist.

Preferred selective CYP2J2 antagonists in context of the present invention are selected from the group of the herein newly disclosed CYP2J2 antagonists consisting of estradiol, phenoxybenzamine-HCl, loratadine, clobetasol propionate, doxazosin mesylate, fenofibrate, levonorgestrel, aripiprazole, halcinonide, telmisartan, clofazimine, levothyroxine-Na, alosetron-HCl, fluocinonide, liothyronine-Na, meclizine dihydrochloride and terfenadine and derivatives thereof.

In context of the herein described invention said pain to be treated is preferably neuropathic pain (including pain associated with diabetic neuropathy, postherpetic neuralgia, HIV/AIDS induced neuropathic pain, traumatic injury, complex regional pain syndrome, trigeminal neuralgia, erythromelalgia and phantom pain), pain produced by mixed nociceptive and/or neuropathic mixed etiologies (e.g., cancer), osteoarthritis, fibromyalgia, lower back pain, inflammatory hyperalgesia, vulvar vestibulitis or vulvodynia, sinus polyps interstitial cystitis, neurogenic or overactive bladder, prostatic hyperplasia, rhinitis, surgery, trauma, rectal hypersensitivity, burning mouth syndrome, oral mucositis, herpes (or other viral infections), prostatic hypertrophy, dermatitis, pruritis, itch, tinnitus, psoriasis, warts, cancers, headaches, and wrinkles, central pain due to stroke or mass lesion, spinal cord injury, or multiple sclerosis. However, most preferred embodiments pertain to chemotherapy-induced peripheral neuropathic pain (CIPNP).

The present invention now provides a pain therapy comprising the inhibition of the activity of in particular CYP2J2 which produces the metabolic compound 9,10-EpOME—according to the invention, a sensitizer of ion channel-mediated pain perception. Surprisingly, the inhibition of CYP2J2 in accordance with the invention proved to be effective in-vivo to alleviate neuropathic pain induced by paclitaxel in a mouse model, indicating the use of CYP2J2 antagonists as analgesic against neuropathic pain, in particular CIPNP.

One further embodiment of the invention relates to the above mentioned prevention or treatment of pain, which comprises the administration of said CYP antagonist of the invention to a subject suffering from said pain, and wherein said subject received, receives or will receive chemotherapy. Therefore, the subject is in preferred embodiments a subject suffering from, or diagnosed with, a cancer disease.

Chemotherapy in context of the invention preferably involves the administration of a chemotherapeutic agent to a subject in need of such a treatment selected from pyrimidinone-based anti-neoplastic agents such as cytarabine, 5-flurouracil or platin agents, such as cisplatin, or taxanes, such as paclitaxel, docetaxel or cabazitaxel, or derivatives thereof. Such chemotherapeutic agents are known to induce neuropathic pain, in particular this is known for taxanes, which are therefore preferred in context of the invention. Most preferred is paclitaxel.

Further, said prevention or treatment of pain in accordance with the invention comprises the concomitant or sequential administration of said CYP antagonist and said chemotherapeutic agent. See for this embodiment also the description below for a combination of the invention.

The problem of the invention is solved in another aspect by a 9,10-epoxy-12Z-octadecenoic acid (9,10-EpOME)-antagonist for use in the prevention or treatment of pain in a subject. 9,10-EpOME was found to be generated by CYP activity. Therefore, instead of antagonizing CYP, the inventive result may be alternatively achieved by antagonizing the 9,10-EpOME directly in order to avoid a sensitization of pain mediating neurons. Such 9,10-EpOME-antagonists of the invention are preferably small molecules but also proteins or peptides (e.g. antibodies or fragments thereof) binding to 9,10-EpOME and inhibiting the sensitization of TRPV1.

For this aspects the above described specific embodiments for the use of CYP antagonists apply also for 9,10-EpOMEantagonists of the invention, in particular the embodiments relating to said prevention or treatment and the chemotherapy.

The problem is additionally solved by a combination comprising (i) a CYP antagonist or an 9,10-EpOME-antagonist and (ii) a chemotherapeutic agent for concomitant or sequential use in the prevention or treatment of a disease, wherein the disease is selected from a proliferative disorder, such as cancer, or pain, such as CIPNP.

The term "proliferative disorder" is used herein in a broad sense to include any disorder that requires control of the cell cycle, for example cardiovascular disorders such as restenosis and cardiomyopathy, auto-immune disorders such as glomerulonephritis and rheumatoid arthritis, dermatological disorders such as psoriasis, anti-inflammatory, antifungal, antiparasitic disorders such as malaria, emphysema and alopecia. In these disorders, the compounds of the present invention may induce apoptosis or maintain stasis within the desired cells as required. Preferably, the proliferative disorder is a cancer or leukemia, most preferably cancer of the breast, lung, prostate, bladder, head and neck, colon, ovarian cancer, uterine cancer, sarcoma or lymphoma.

The present embodiment also relates to the treatment of a subject group suffering from pain, wherein the subjects are under the treatment with a chemotherapeutic. The CYP-antagonist of the invention therefore may be administered during the same period of time as the cancer treatment, or alternatively is done before or after, which can be preferable in order to avoid accumulating adverse effects. The inventive result is achieved when the physiological effects of a CYP-antagonist of the invention and the pain inducement of a chemotherapeutic are combined in a subject in need of such a treatment. After the last dose of a medicament is administered during therapy, the physiological effects induced by the medicament will not diminish immediately, but most likely later. Therefore, using the antagonists of the invention in sequential therapeutic cycles, for example the antagonists of the invention are administered in advance of a chemotherapy instead at the same time, still leads to a combination of the clinical effects of both compounds in the patient, and therefore falls under the meaning of the combination therapy of the present invention.

The term "combination" means in this context an active substance combination of two or more active substances in a formulation and also as a combination in the sense of individual formulations of the active substances administered at specified intervals from one another in a therapeutic treatment. Thus the term "combination" shall include the clinical reality of a co-administration of two or more therapeutically effective compounds, as it is described in context of the present invention.

Co-administration: In the context of the present application, co-administration of two or more compounds is defined as administration of the two or more compounds to the patient within one year, including separate administration of two or more medicaments each containing one of the compounds as well as simultaneous administration whether or not the two or more compounds are combined in one formulation or whether they are in two or more separate formulations.

The combination of the invention in one embodiment includes that (i) and (ii) are combined by sequential or concomitant administration to a subject during said prevention or treatment, preferably wherein the antagonists and chemotherapeutics are concomitantly administered during said prevention or treatment.

A chemotherapeutic is preferably selected from pyrimidinone-based anti-neoplastic agents such as cytarabine, 5-flurouracil or platin agents, such as cisplatin, or taxanes, such as paclitaxel or docetaxel, or derivatives thereof. Most preferably the chemotherapeutic is paclitaxel or docetaxel.

Antagonists of the herein described invention are preferably selected from the group of compounds consisting of inhibitory RNA, inhibitory antibodies or fragments thereof, and/or small molecules. Herein below a detailed description of preferred CYP-antagonists is provided.

In context of the invention it is also preferred that at least one additional therapeutic effective against pain, for example a morphine, an opioid or a non-opioid analgesic or other analgesic, is administered to said subject.

In another aspect of the invention there is provided a method for the prevention or treatment of pain in a subject, the method comprising the step of administering to said subject a therapeutically effective amount of a CYP-antagonist or a 9,10-EpOME-antagonist in accordance with the present invention. The CYP-antagonist is preferably selected from the group consisting of a CYP1A-, CYP2B-, CYP2C-, CYP2E-, and CYP2J-antagonist. The CYP2J-antagonist is preferably an antagonist of a mammalian homologue of CYP2J2 (CYP2J2-antagonist), preferably, human CYP2J2, such as terfenadine or telmisartan, as well as biosimilars or derivatives thereof.

Other preferred CYP antagonists are selected from the group consisting of estradiol, phenoxybenzamine-HCl, loratadine, clobetasol propionate, doxazosin mesylate, fenofibrate, levonorgestrel, aripiprazole, halcinonide, telmisartan, clofazimine, levothyroxine-Na, alosetron-HCl, fluocinonide, liothyronine-Na, meclizine dihydrochloride and terfenadine.

The diseases treatable in context of the afore-described methods are described herein above.

During the treatment or prevention it is preferred that at least one additional therapeutic effective against pain is administered to said patient, such as other analgesics, for example an opioid or a non-opioid analgesic.

An additional aspect of the invention then relates to a method for increasing sensitivity of Transient Receptor Potential Vanilloid 1 (TRPV1) in a subject, comprising administering to said subject a therapeutically effective amount of 9,10-EpOME or of an CYP2J2 agonist.

In context of the invention is was surprisingly found that 9,10-EpOME sensitises the TRPV1 channel protein, which is a major mediator of pain perception. Therefore, the present invention in a preferred embodiment provides 9,10-EpOME as an TRPV1 agonist, which is particularly useful in medicine. Combinations of 9,10-EpOME and the TRPV1 agonist capsaicin significantly enhanced capsaicin activity. One embodiment for example pertains to the treatment of a disease characterized by a pathological suppressed sensation of pain or insensitivity of pain.

In another embodiment 9,10-EpOME may be used in a method for enhancing the activity of TRPV1-agonists, such as capsaicin. Capsaicin is used as an analgesic in topical ointments, nasal sprays, and dermal patches to relieve pain. It may be applied in cream form for the temporary relief of minor aches and pains of muscles and joints associated with arthritis, backache, strains and sprains, often in compounds with other rubefacients. It is also used to reduce the symptoms of peripheral neuropathy such as post-herpetic neuralgia caused by shingles.

The mechanism by which capsaicin's analgesic and/or anti-inflammatory effects occurs is purportedly by mimicking a burning sensation; overwhelming the nerves by the calcium influx, leading to desensitisation and/or apoptosis of nociceptors and thereby rendering the nerves unable to report pain for an extended period of time. With chronic exposure to capsaicin, nociceptors of neurons underwent apoptosis, leading to reduction in sensation of pain and blockade of neurogenic inflammation. If capsaicin is removed, the nociceptive neurons recover over time. Therefore, the use of 9,10-EpOME of the invention may greatly increase the medical effects of capsaicin and related compounds, or alternatively may help to reduce capsaicin dosing.

Therefore, in a preferred embodiment of the invention there is provided a method for treating a disease in a subject, comprising the administration of a therapeutically effective amount of (i) 9,10-EpOME or of an CYP2J2 agonists, and (ii) an TRPV1 agonist. With regard to sequential or concomitant uses of therapeutics, reference is made to the above descriptions which equally apply for this aspect of the invention.

A disease is preferably selected from neuropathic pain (including pain associated with diabetic neuropathy, postherpetic neuralgia, HIV/AIDS, traumatic injury, complex regional pain syndrome, trigeminal neuralgia, erythromelalgia and phantom pain), pain produced by mixed nociceptive and/or neuropathic mixed etiologies (e.g., cancer), osteoarthritis, fibromyalgia, lower back pain, inflammatory hyperalgesia, vulvar vestibulitis or vulvodynia, sinus polyps interstitial cystitis, neurogenic or overactive bladder, prostatic hyperplasia, rhinitis, surgery, trauma, rectal hypersensitivity, burning mouth syndrome, oral mucositis, herpes (or other viral infections), prostatic hypertrophy, dermatitis, pruritis, itch, tinnitus, psoriasis, warts, cancers, headaches, and wrinkles. Generally any disease is comprised which is treatable by an TRPV1 agonist.

Exemplary and preferred TRPV1 agonist of the invention are selected from the group consisting of capsaicin, piperine, 6-gingerol, 6-shogaol, α-sanshool, β-sanshool, γ-sanshool, δ-sanshool, hydroxyl α-sanshool, and hydroxyl β-sanshool.

Another aspect then pertains to a 9,10-EpOME or an CYP2J2 agonists for use in a method as described herein above.

Yet another aspect pertains to a combination of (i) 9,10-EpOME or of an CYP2J2 agonist, and (ii) an TRPV1 agonist, for use in medicine, preferably in the treatment of a disease selected from neuropathic pain (including pain associated with diabetic neuropathy, postherpetic neuralgia, HIV/AIDS, traumatic injury, complex regional pain syndrome, trigeminal neuralgia, erythromelalgia and phantom pain), pain produced by mixed nociceptive and/or neuropathic mixed etiologies (e.g., cancer), osteoarthritis, fibromyalgia, lower back pain, inflammatory hyperalgesia, vulvar vestibulitis or vulvodynia, sinus polyps interstitial cystitis, neurogenic or overactive bladder, prostatic hyperplasia, rhinitis, surgery, trauma, rectal hypersensitivity, burning mouth syndrome, oral mucositis, herpes (or other viral infections), prostatic hypertrophy, dermatitis, pruritis, itch, tinnitus, psoriasis, warts, cancers (especially skin cancers), headaches, and wrinkles.

The TRPV1 agonist is preferably selected from the group consisting of capsaicin, piperine, 6-gingerol, 6-shogaol, α-sanshool, β-sanshool, γ-sanshool, δ-sanshool, hydroxyl α-sanshool, and hydroxyl β-sanshool.

A subject in accordance with the herein described invention is preferably a mammal, preferably a human, most preferably a human receiving a chemotherapeutic treatment, such as a cancer patient.

CYP-Antagonists

"CYP antagonists" in context of the present invention are preferably selected from the group consisting of a CYP1A-, CYP2B-, CYP2C-, CYP2E-, and more preferably a CYP2J-antagonist. Most preferably the CYP-antagonist is an antagonist of a mammalian homologue of CYP2J2 (CYP2J2-antagonist), preferably human CYP2J2. Therefore, in most preferred embodiments and aspects of the herein described invention the term "CYP-antagonist" is a CYP2J2 antagonists, or antagonists of mammalian homologs of human CYP2J2.

As used herein, the term "CYP-antagonist" means a substance that affects a decrease in the amount or rate of CYP expression or activity. Such a substance can act directly, for example, by binding to CYP and decreasing the amount or rate of CYP expression or activity. A CYP-antagonist can also decrease the amount or rate of CYP expression or activity, for example, by binding to CYP in such a way as to reduce or prevent interaction of CYP with a CYP receptor; by binding to CYP and modifying it, such as by removal or addition of a moiety; and by binding to CYP and reducing its stability. A CYP-antagonist can also act indirectly, for example, by binding to a regulatory molecule or gene region so as to modulate regulatory protein or gene region function and affect a decrease in the amount or rate of CYP expression or activity. Thus, a CYP-antagonist can act by any mechanisms that result in decrease in the amount or rate of CYP expression or activity.

A CYP-antagonist can be, for example, a naturally or non-naturally occurring macromolecule, such as a polypeptide, peptide, peptidomimetic, nucleic acid, carbohydrate or lipid. A CYP-antagonist further can be an antibody, or antigen-binding fragment thereof, such as a monoclonal antibody, humanized or human antibody, chimeric antibody, minibody, bifunctional antibody, single chain antibody (scFv), variable region fragment (Fv or Fd), Fab or F(ab)2. A CYP-antagonist can also be polyclonal antibodies specific for CYP. A CYP-antagonist further can be a partially or completely synthetic derivative, analog or mimetic of a naturally occurring macromolecule, or a small organic or inorganic molecule.

A CYP-antagonist that is an antibody can be, for example, an antibody that binds to CYP and inhibits binding to a CYP receptor, or alters the activity of a molecule that regulates CYP expression or activity, such that the amount or rate of CYP expression or activity is decreased. An antibody useful in a method of the invention can be a naturally occurring antibody, including a monoclonal or polyclonal antibodies or fragment thereof, or a non-naturally occurring antibody, including but not limited to a single chain antibody, chimeric antibody, bifunctional antibody, complementarity determining region-grafted (CDR-grafted) antibody and humanized antibody or an antigen-binding fragment thereof.

A CYP-antagonist that is a nucleic acid can be, for example, an anti-sense nucleotide sequence, an RNA molecule, or an aptamer sequence. An anti-sense nucleotide sequence can bind to a nucleotide sequence within a cell and modulate the level of expression of CYP, or modulate expression of another gene that controls the expression or activity of CYP. Similarly, an RNA molecule, such as a catalytic ribozyme, can bind to and alter the expression of the CYP gene, or other gene that controls the expression or activity of CYP. An aptamer is a nucleic acid sequence that has a three dimensional structure capable of binding to a molecular target.

A CYP-antagonist that is a nucleic acid also can be a double-stranded RNA molecule for use in RNA interference methods. RNA interference (RNAi) is a process of sequence-specific gene silencing by post-transcriptional RNA degradation, which is initiated by double-stranded RNA (dsRNA) homologous in sequence to the silenced gene. A suitable double-stranded RNA (dsRNA) for RNAi contains sense and antisense strands of about 21 contiguous nucleotides corresponding to the gene to be targeted that form 19 RNA base pairs, leaving overhangs of two nucleotides at each 3' end (Elbashir et al., Nature 411:494-498 (2001); Bass, Nature 411:428-429 (2001); Zamore, Nat. Struct. Biol. 8:746-750 (2001)). dsRNAs of about 25-30 nucleotides have also been used successfully for RNAi (Karabinos et al., Proc. Natl. Acad. Sci. USA 98:7863-7868 (2001). dsRNA can be synthesized in vitro and introduced into a cell by methods known in the art.

Preferred CYP2J2 antagonists are selected from the group consisting of estradiol, phenoxybenzamine-HCl, loratadine, clobetasol propionate, doxazosin mesylate, fenofibrate, levonorgestrel, aripiprazole, halcinonide, telmisartan, clofazimine, levothyroxine-Na, alosetron-HCl, fluocinonide, liothyronine-Na, meclizine dihydrochloride and terfenadine.

Compositions and Kits for Treating or Preventing Pain or Other Neurological Disorders Another aspect of the present application relates to compositions and kits for treating or preventing pain or proliferative disorder by using the compounds or combinations of the invention. In one embodiment, the composition comprises compounds as described herein above, wherein the compounds are preferably selected from an antibody, antibody fragment, short interfering RNA (siRNA), aptamer, synbody, binding agent, peptide, aptamer-siRNA chimera, single stranded antisense oligonucleotide, triplex forming oligonucleotide, ribozyme, external guide sequence, agent-encoding expression vector, small molecule and a pharmaceutically acceptable carrier.

As used herein the language "pharmaceutically acceptable carrier" is intended to include any and all solvents, solubilizers, fillers, stabilizers, binders, absorbents, bases, buffering agents, lubricants, controlled release vehicles, diluents, emulsifying agents, humectants, lubricants, dispersion media, coatings, antibacterial or antifungal agents, isotonic and absorption delaying agents, and the like, compatible with pharmaceutical administration. The use of such media and agents for pharmaceutically active substances is well-known in the art. Except insofar as any conventional media or agent is incompatible with the active compound, use thereof in the compositions is contemplated. Supplementary agents can also be incorporated into the compositions. In certain embodiments, the pharmaceutically acceptable carrier comprises serum albumin.

The pharmaceutical composition of the invention is formulated to be compatible with its intended route of administration. Examples of routes of administration include parenteral, e.g., intrathecal, intra-arterial, intravenous, intradermal, subcutaneous, oral, transdermal (topical) and transmucosal administration.

Solutions or suspensions used for parenteral, intradermal, or subcutaneous application can include the following components: a sterile diluent such as water for injection, saline solution fixed oils, polyethylene glycols, glycerine; propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the injectable composition should be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the requited particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a neuregulin) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Stertes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the pharmaceutical compositions are formulated into ointments, salves, gels, or creams as generally known in the art.

In certain embodiments, the pharmaceutical composition is formulated for sustained or controlled release of the active ingredient. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from e.g. Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art.

It is especially advantageous to formulate oral or parenteral compositions in dosage unit form for ease of administration and uniformity of dosage. Dosage unit form as used herein includes physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. The pharmaceutical compositions can be included in a container, pack, or dispenser together with instructions for administration.

The present invention will now be further described in the following examples with reference to the accompanying figures and sequences, nevertheless, without being limited thereto. For the purposes of the present invention, all references as cited herein are incorporated by reference in their entireties. In the Figures:

FIG. 1: Concentrations of oxidized linoleic acid metabolites during paclitaxel CIPNP or inflammation. Shown are the concentrations of 9,10-EpOME (a) and 12,13-EpOME (b) in sciatic nerves, DRG and the spinal dorsal horn 24 h after i.p. injection of vehicle (black) or paclitaxel (grey, 6 mg·kg-1) in C57Bl6/N mice; n.d.: not determined. Concentrations of 9-HODE (c) and 13-HODE (d) in sciatic nerves, L4-L6-DRGs and the corresponding section of the spinal dorsal horn 24 h after i.p. injection of vehicle (black) or paclitaxel (grey) in C57Bl6/N mice. (e) Relation of 9,10-EpOME-concentrations in L4-L6-DRGs and the corresponding section of the dorsal horn 24 h after intraplar injection of zymosan (12.5 mg/ml, 20 µl) Data represent the mean ±SEM of 8-10 animals per group; ***p<0.001, student's t-test.

Figure 2:
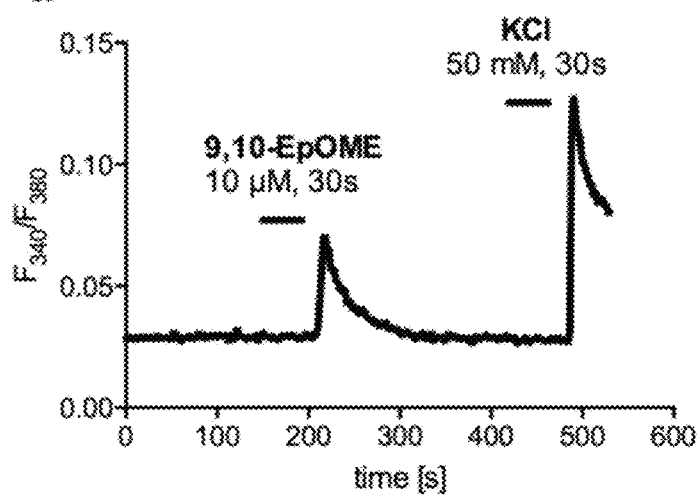
Figure 2:
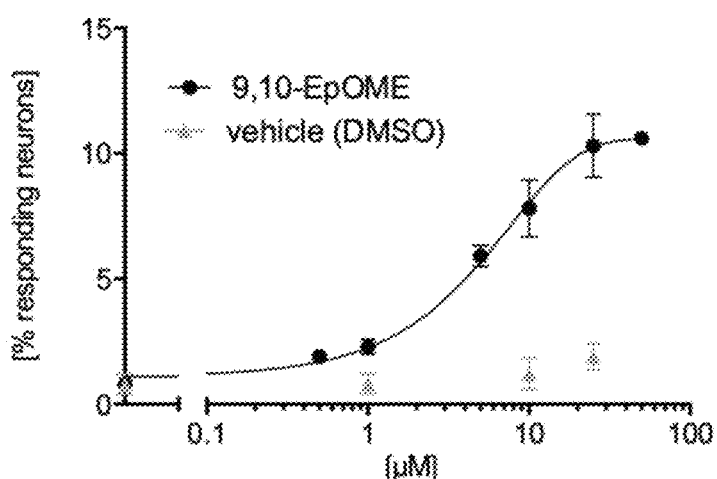
Figure 2:
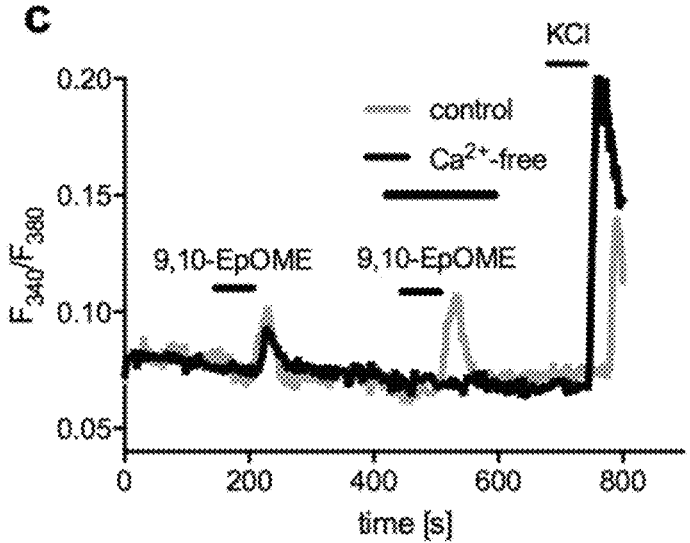
Figure 2:
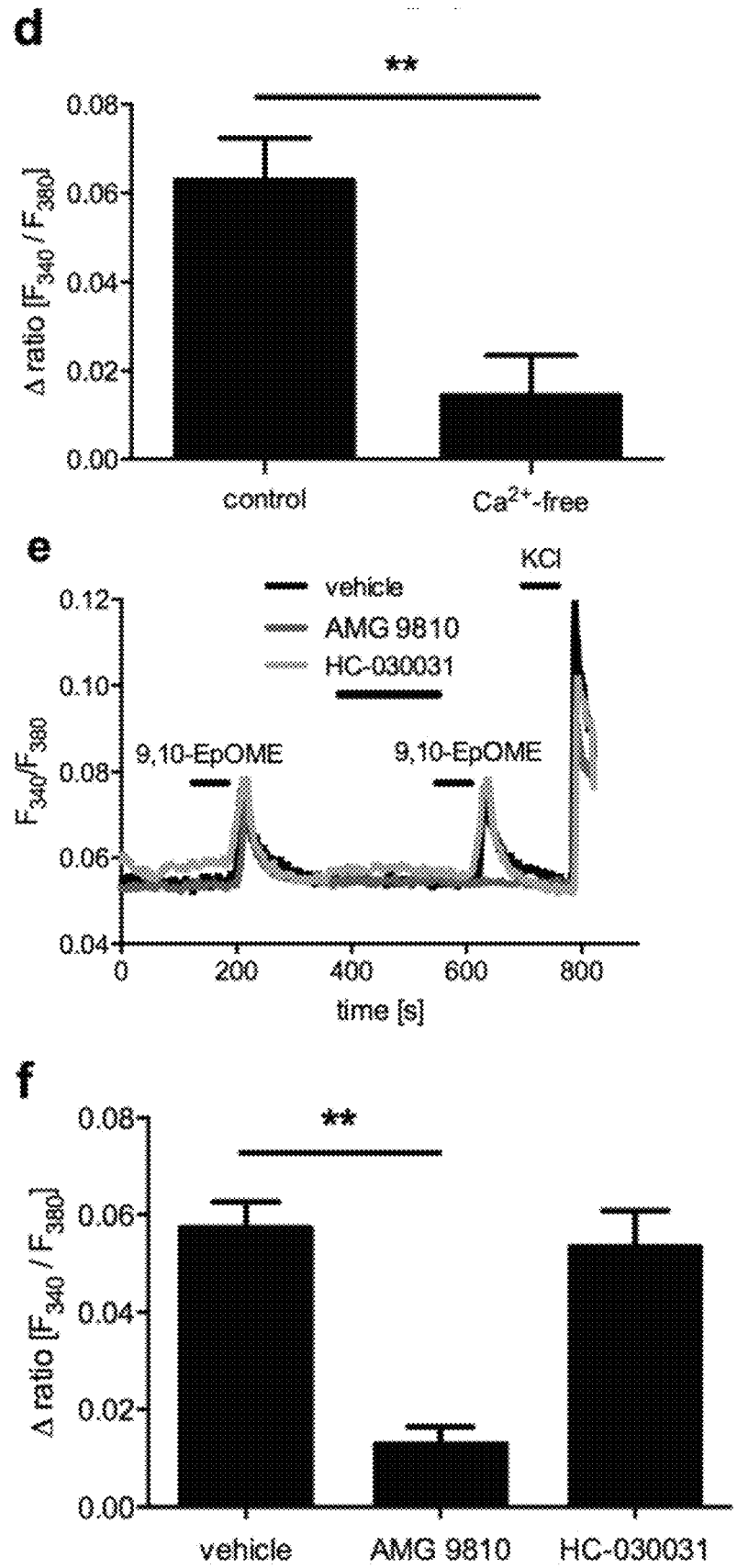

FIG. 2: Direct effects of 9,10-EpOME on DRG-neurons. (a) Application of 9,10-EpOME [10 µM, 30 s] causes calcium transients on DRG neurons which respond to high potassium (50 mM KCl, 30 s). A representative trace is shown. (b) Dose response relationship of 9,10-EpOME dependent calcium increases in DRG neurons related to the number of responding neurons Data represents the mean ±SEM of five measurements per concentration. (c) and (d) Calcium transients caused by 9,10-EpOME [10 µM, 30 s] can be disrupted using calcium-free medium containing EGTA (2 mM) washed in 2 minutes before and after 9,10-EpOME stimulation. Data represents the mean ±SEM of 24 (calcium-free) or 16 (control) neurons. (e) and (f) Calcium transients of 9,10-EpOME [10 µM, 30 s] can be blocked by a selective TRPV1 antagonist (AMG 9810, 1 µM) but not by a selective TRPA1 antagonist (HC-030031, 20 µM) washed in for two minutes prior to the second 9,10-EpOME stimulation. Data represents the mean ±SEM of 16 (control), 31 (AMG 9810) or 18 (HC-030031) neurons; **p<0.01, student's t-test.

Figure 3:
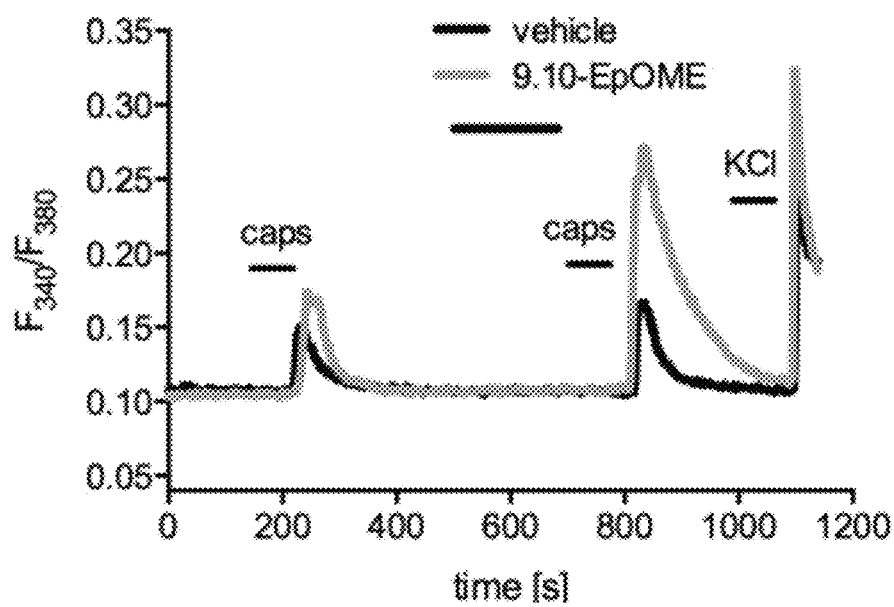
Figure 3:
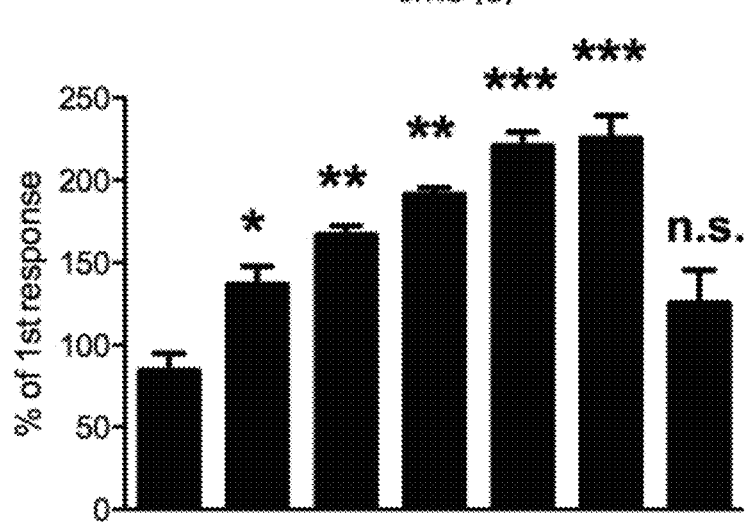
Figure 3:
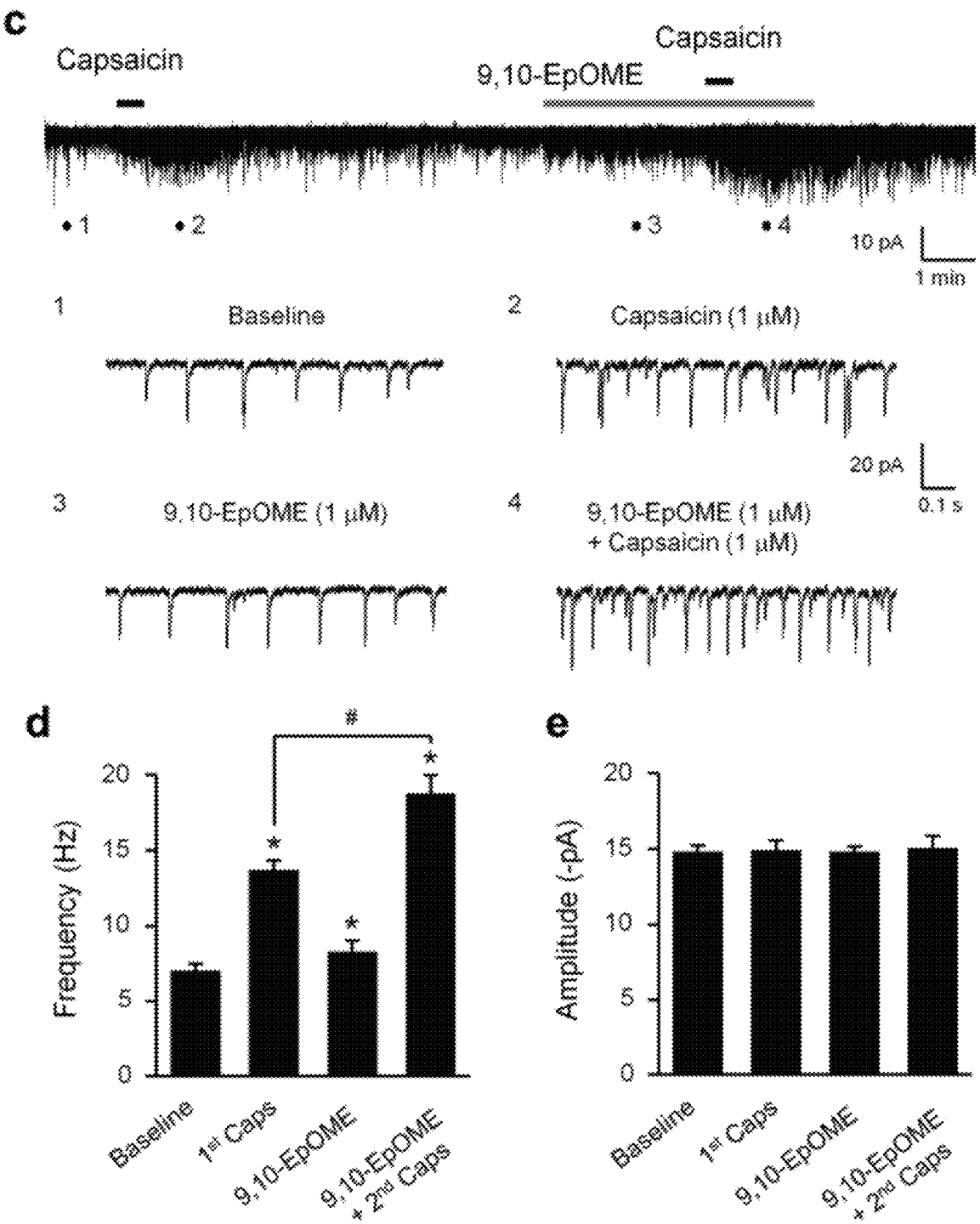

FIG. 3: 9,10-EpOME dose-dependently sensitizes TRPV1 in DRG neurons and potentiates capsaicin-induced increases in spontaneous EPSC frequency in lamina II neurons of spinal cord slices. (a) DRG neurons were double-stimulated with capsaicin (200 nM, 15 s each) and incubated with either vehicle or 9,10-EpOME [1 µM] for two minutes prior to the second capsaicin stimulation. (b) Dose-dependent difference in ratio between the first and the second capsaicin response using the same protocol as described in (a). Data represent the mean ±SEM of the following number of neurons: 27 (control), 26 (250 nM 9,10-EpOME), 21 (500 nM 9,10-EpOME), 19 (750 nM 9,10-EpOME), 41 (1 µM 9,10-EpOME), 18 (2 µM 9,10-EpOME) or 28 (using 50 µM AITC for 20 s instead of capsaicin); *p<0.05, p<0.01, *p<0.001 student's t-test. (c) Traces of spontaneous EPSCs (sEPSCs) in lamina II neurons. Low panel, traces 1, 2, 3, and 4 are enlarged and indicate recordings of baseline, 1st capsaicin (1 mM), 9,10-EpOME (1 mM), and 2nd capsaicin (1 mM) plus 9,10-EpOME, respectively. (d) Frequency of sEPSCs. Compared to baseline of sEPSCs, capsaicin induced profound increases in sEPSC frequency (from 6.9±0.4 Hz and 13.7±0.4 Hz). Treatment of 9,10-EpOME alone slightly increased the frequency of sEPSCs (8.2±0.8 Hz) and significantly potentiated the sEPSC frequency increase by capsaicin (18.7±1.1 Hz). *$P<0.05$, compared with no treatment baseline; #$P<0.05$, compared with 1st capsaicin treatment (1 mM). n=5 neurons/group. (E) Amplitude of sEPSCs. Capsaicin and 9,10-EpOME had no significant effects on sEPSC amplitude. n=5 neurons/group.

Figure 4:
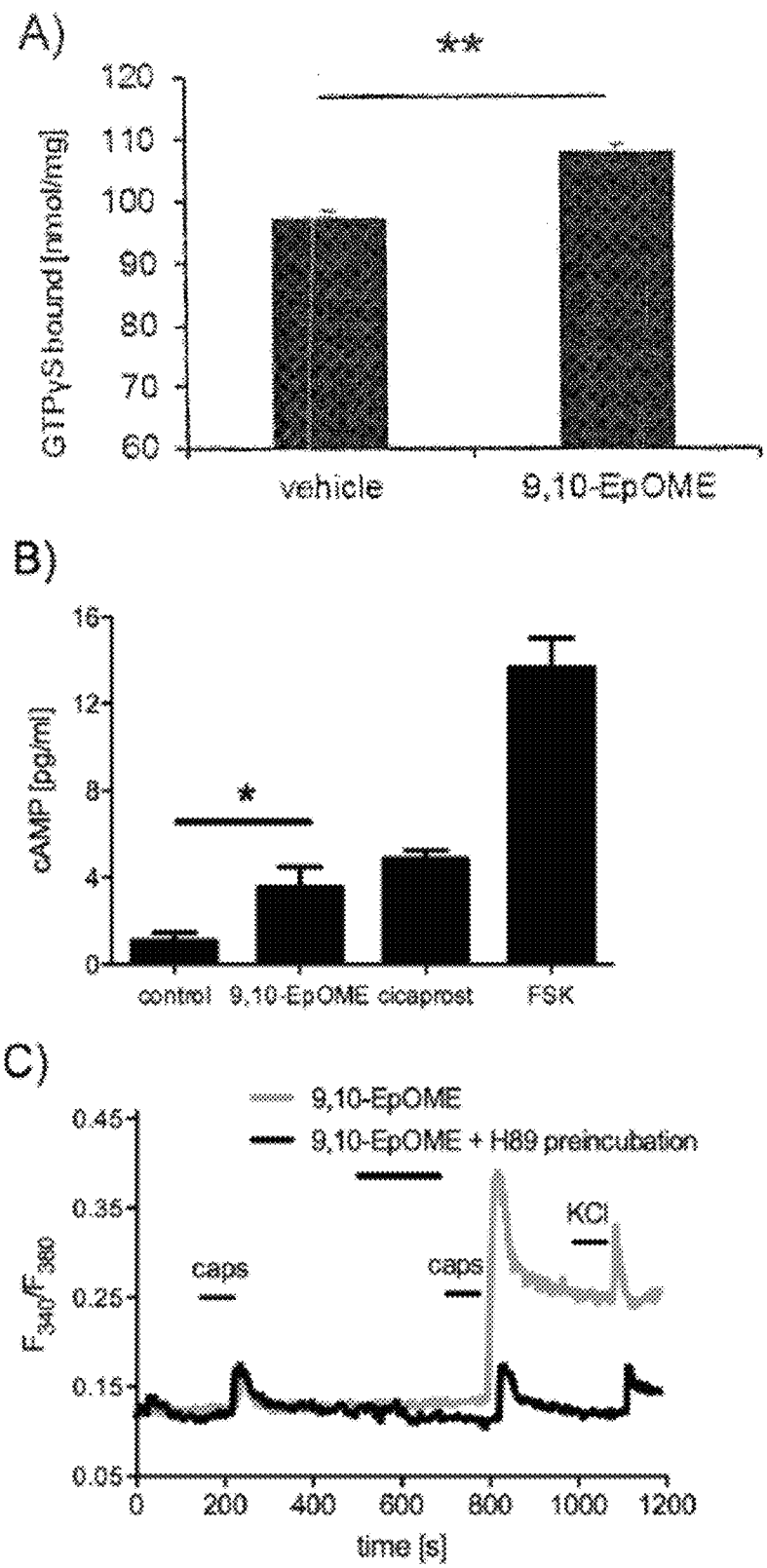
Figure 4:
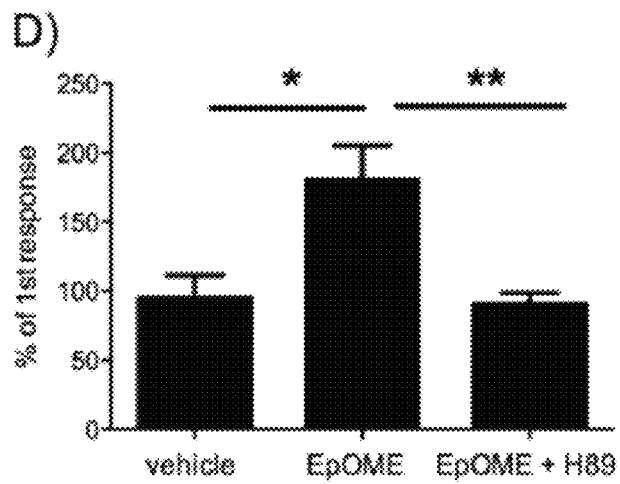
Figure 4:
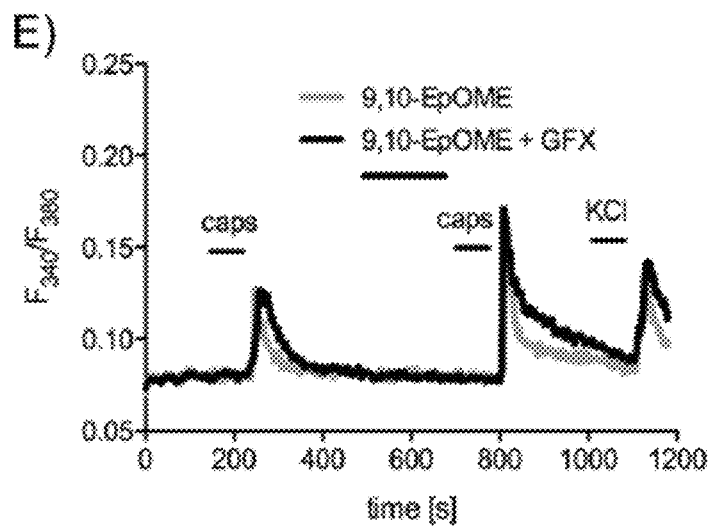
Figure 4:
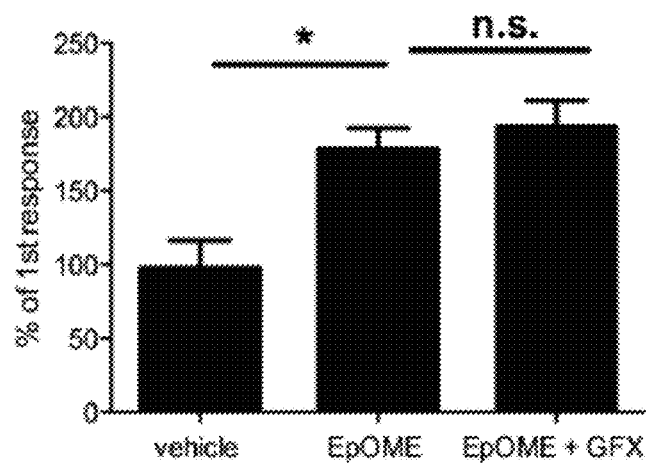

FIG. 4: TRPV1-sensitization by 9,10-EpOME in DRG neurons is mediated by a Gs-coupled receptor and the cAMP-PKA pathway. (a) 9,10-EpOME catalyzed the [γ-35S]-GTP binding in membrane fractions of rat DRGs. Experiments were carried out using membrane fractions of rat DRGs in the presence of 30 µM GDP and vehicle (Methyl Acetate. 0.7% (v/v)), adenosine [10 µM] or 9,10-EpOME [1 µM] for 30 minutes. The data were obtained from 3 measurements of membrane fractions from a total of 15 animals. DRGs from five animals were pooled for each measurement; *$p<0.05$, **$p<0.01$, Kruskal-Wallis test with Dunn's multiple comparison post hoc test. (b) Concentrations of cAMP in neuron-enriched DRG cultures after stimulation with 9,10-EpOME, cicaprost or forskolin (1 µM each) for 15 minutes. Data represents mean ±SEM of DRG cultures from from five mice. (c) and (d) TRPV1 sensitization by 9,10-EpOME [1 µM] can be reduced by preincubation with a PKA-inhibitor (H89-dihydrochloride, 10 µM for 1 h). Data represent mean ±SEM of 15 (vehicle), 19 (EpOME) or 33 neurons (EpOME with H89 preincubation). (e) and (f) TRPV1 sensitization by 9,10-EpOME [1 µM] is not affected by preincubation with a PKC-inhibitor (GF 109203X, 10 µM for 1 h). Data represent mean ±SEM of 18 (vehicle), 23 (EpOME) or 39 neurons (EpOME with GFX preincubation); *$p<0.05$, **$p<0.01$ student's t-test; n.s. not significant.

Figure 5:
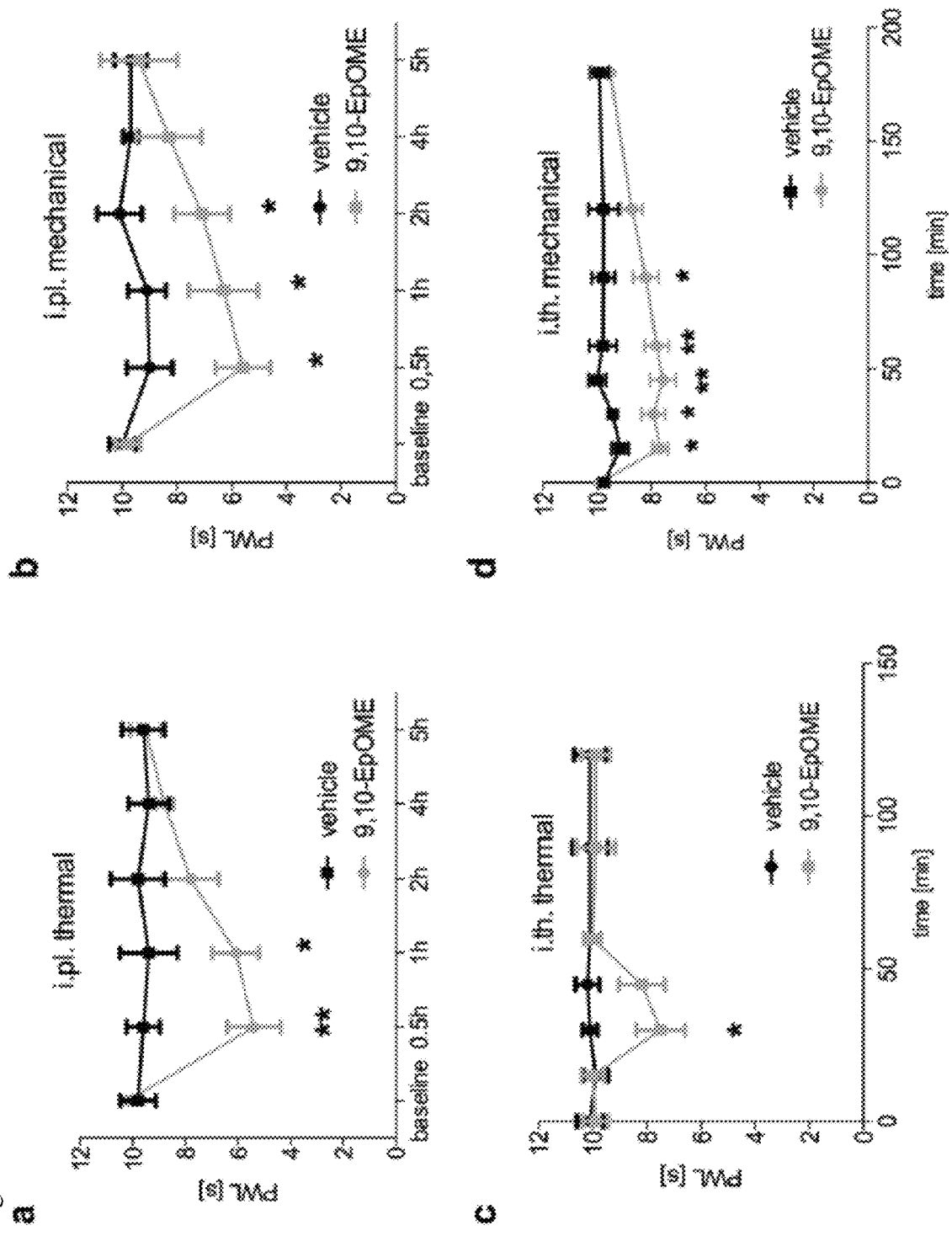
Figure 6:
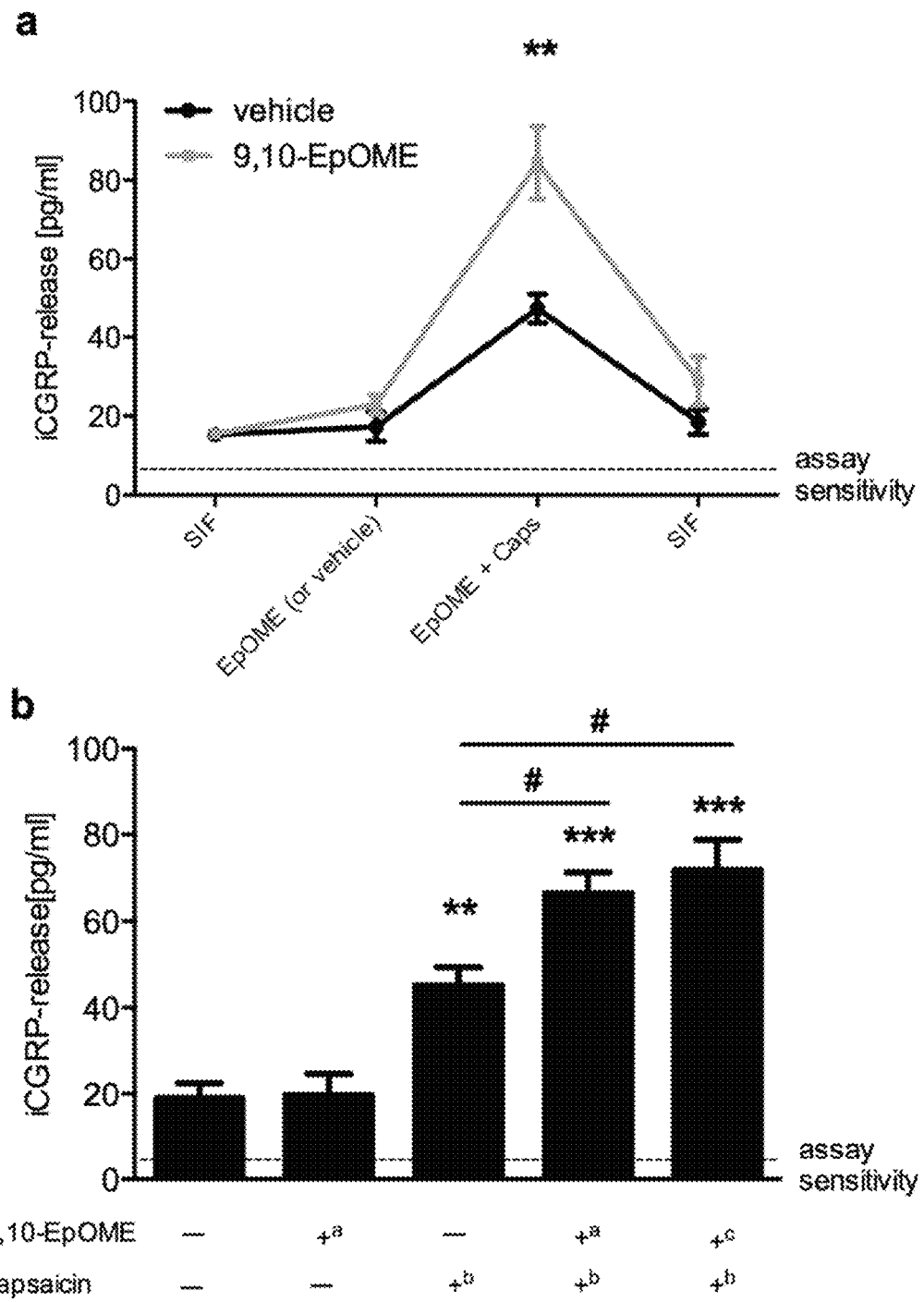

FIG. 5: Intraplantar or intrathecal injection of 9,10-EpOME reduces pain thresholds and sensitizes capsaicin induced mechanical thresholds in wild type mice. (a) and (b) C57Bl/6N mice received an intraplantar injection of 9,10-EpOME (10 µM) or vehicle (DMSO 0.3% (v/v) in saline). Thermal (a) or mechanical (b) thresholds were monitored for 5 h post injection. Data represents mean ±SEM from eight mice. (c) and (d) Wild type BL/6N mice were injected intrathecally with 9,10-EpOME (10 µM) or vehicle (DMSO 0.3% (v/v) in saline). Thermal (c) or mechanical (d) thresholds were monitored for 2 h (thermal) or 3 h (mechanical) post injection with 15 minute intervals for the first hour and 30 minute intervals for the second hour. Data represents mean ±SEM from eight mice. Die Abbildungen sind nicht mitgeliefert FIG. 6: Release of iCGRP from isolated sciatic nerves or neuron enriched DRG cultures after 9,10-EpOME stimulation. (a) Release of iCGRP from isolated sciatic nerves of wild type BL/6N mice, stimulated with the following solutions for 5 minutes each: synthetic intestinal fluid (SIF), SIF+EpOME (1 µM) or vehicle (DMSO 0.03% (v/v)), SIF+EpOME (or vehicle)+capsaicin (500 nM), SIF. Data represents mean ±SEM from six individual sciatic nerves. (b) Release of iCGRP from neuron enriched DRG cultures after stimulation with either PBS, 9,10-EpOME, capsaicin or 9,10-EpOME+capsaicin for 15 minutes; a: 9,10-EpOME 1 µM, b: capsaicin 400 nM, c: 9,10-EpOME 2.5 µM. Data represents mean ±SEM of DRG cultures from six mice; #, *$p<0.05$, $p<0.01$, *$p<0.001$ student's t-test. Dashed line indicates assay sensitivity.

Figure 7:
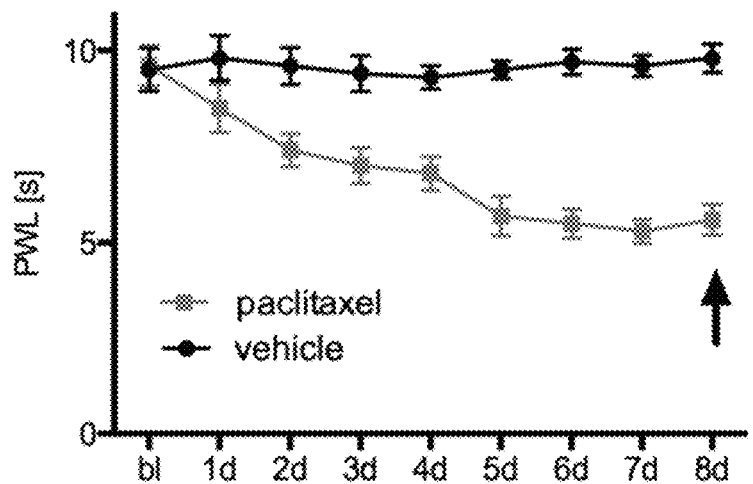
Figure 7:
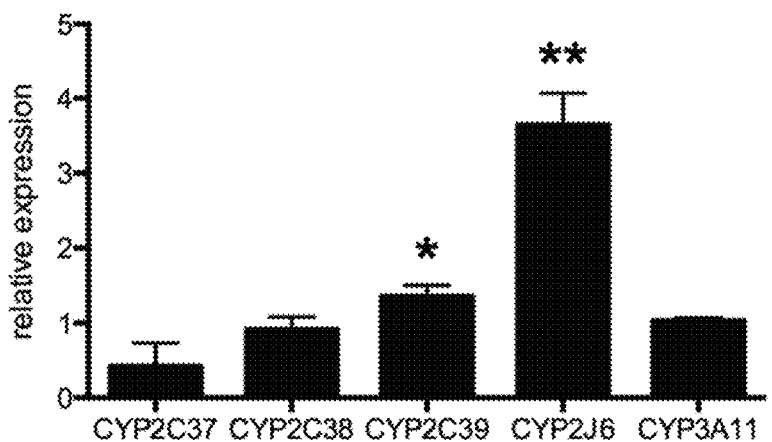
Figure 7:
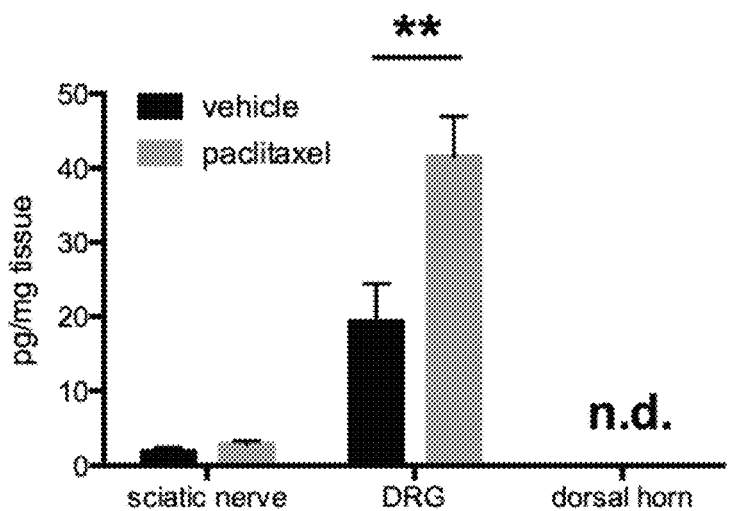
Figure 7:
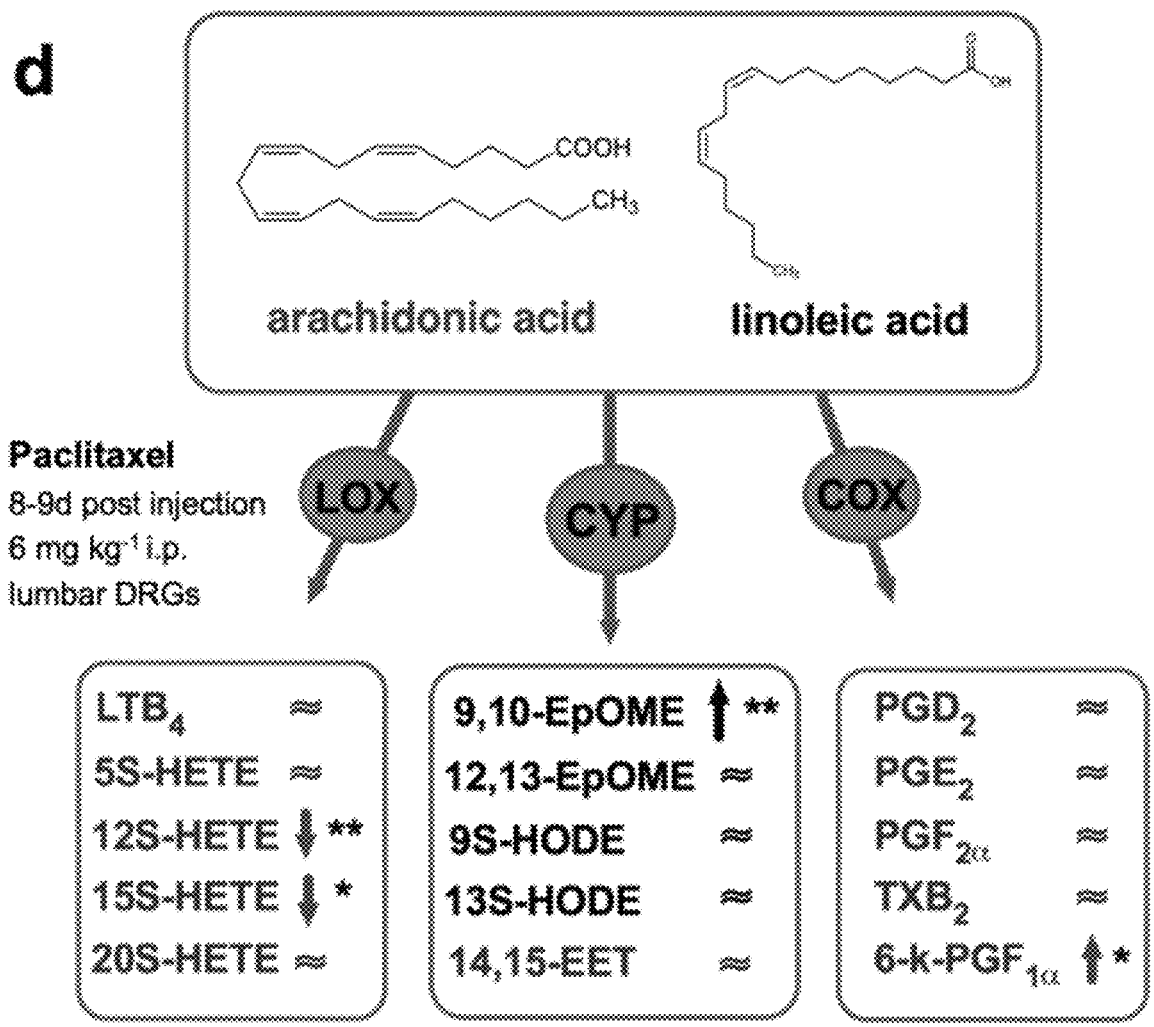

FIG. 7: CYP2J6 is upregulated during paclitaxel-induced neuropathic pain. (a) Time-course of the mechanical thresholds of wild type C57B1/6N-mice after injection of paclitaxel (6 mg·kg-1 i.p.). b1: baseline, data represents mean ±SEM of ten mice per group. After eight days sciatic nerves, DRGs and the spinal dorsal horn were dissected. (b) Expression of murine CYP-epoxygenase-transcripts eight days after paclitaxel-injection (6 mg·kg-1 i.p.). Data represents mean ±SEM from the DRGs of four mice per group, *$p<0.05$, $p<0.01$, student's t-test. (c) Concentrations of 9,10-EpOME in sciatic nerves, DRG and the spinal dorsal horn eight days after i.p. injection of vehicle (black) or paclitaxel (grey, 6 mg·kg-1) in C57B16/N mice; $p<0.01$, student's t-test. (d) Scheme of eicosanoid- and linoleic acid metabolite-synthesis in murine DRGs eight to nine days after paclitaxel-treatment as revealed by LC-MS/MS analysis. Structures were obtained from lipidmaps.org.

Figure 8:
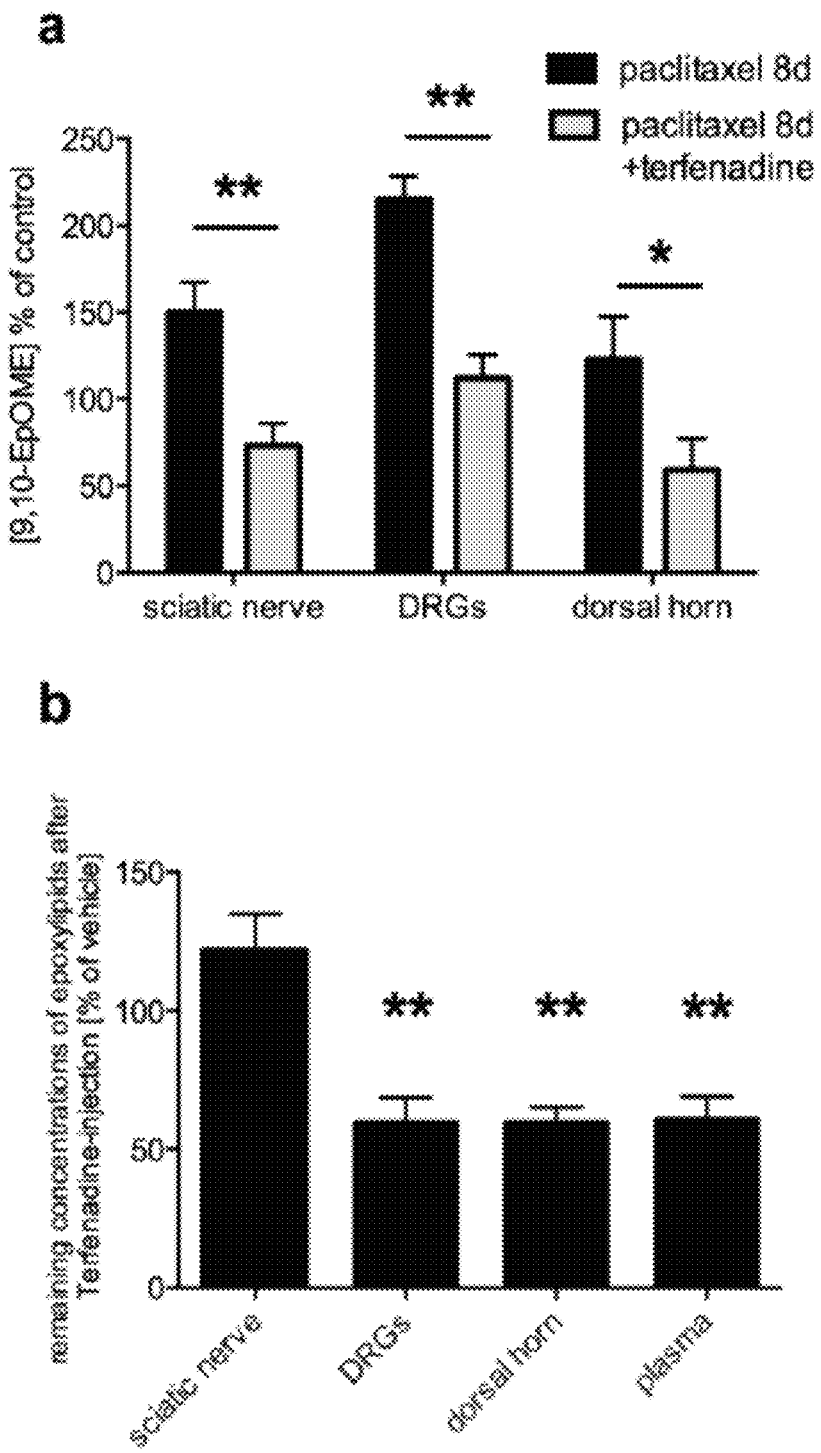
Figure 8:
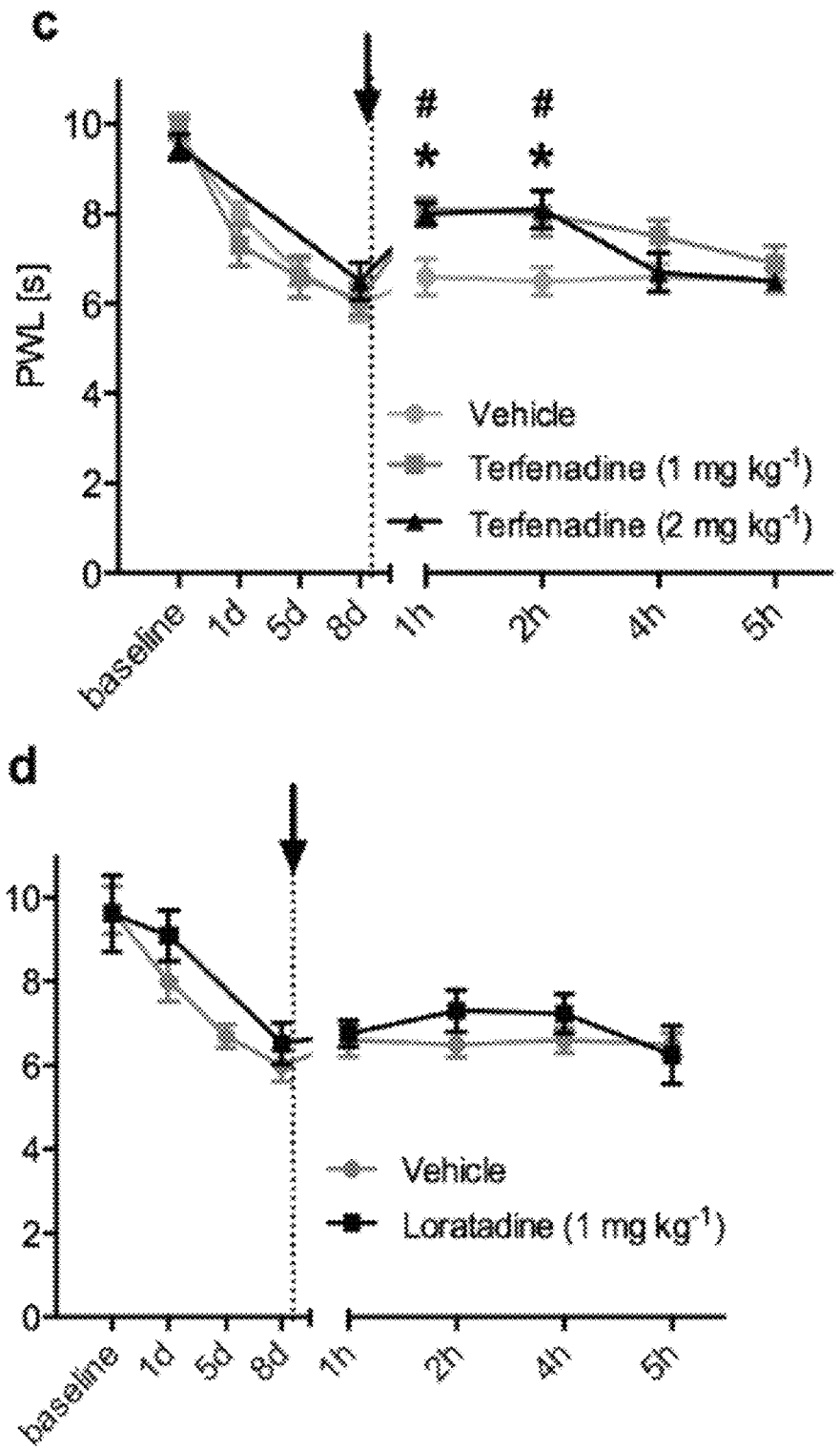

FIG. 8: Inhibition of CYP2J6 by terfenadine reduces lipid concentrations and ameliorates paclitaxel-induced CIPNP in vivo. (a) Levels of 9,10-EpOME shown in % of control determined by LC-MS/MS in sciatic nerves, DRGs and the dorsal horn of the spinal cord eight days after treatment with paclitaxel (6 mg·kg-1 i.p. and 1 mg·kg-1 terfenadine (grey) or vehicle (2% DMSO v/v, black)) Data represents mean ±SEM from the DRGs of five mice per group; *$p<0.05$, **$p<0.01$, student's t-test. (b) Remaining concentrations of all measured epoxylipids and dihydro-metabolites (9,10-EpOME, 12,13-EpOME, 9,10-DiHOME, 12,13-DiHOME and 14,15-EET) in sciatic nerve, DRGs, dorsal horn of the spinal cord and plasma after administration of terfenadine (1 mg·kg-1). (c) Mechanical thresholds of mice treated with paclitaxel for eight days (6 mg·kg-1 i.p.) that received an intravenous injection of terfenadine (1 or 2 mg kg-1) or vehicle (DMSO 2.5 or 5% (v/v)). The mechanical thresholds were monitored up to 5 h after injection of terfenadine or vehicle. Data represent mean ±SEM from 8-9 mice per group; #, *$p<0.05$, two-way ANOVA with Bonferroni post hoc test (*1 mg kg-1, #2 mg kg-1 terfenadine). (d) Mechanical thresholds of mice eight days after paclitaxel-injection (6 mg·kg-1 i.p.) that received an intravenous injection of Loratadine (1 mg kg-1) or vehicle (DMSO (2.5% (v/v)). Data represent mean ±SEM from 6-9 mice per group.

Figure 9:
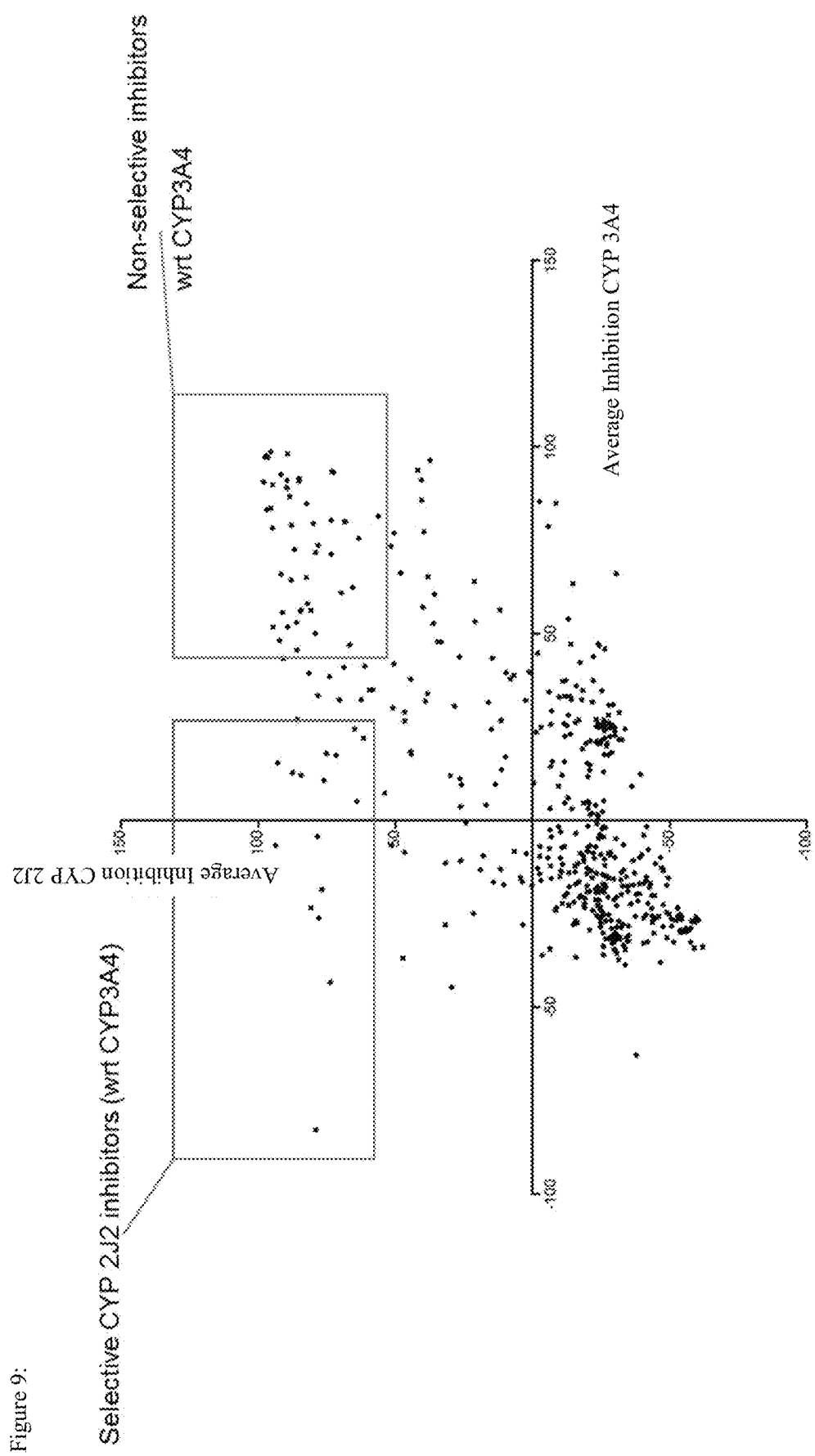

FIG. 9: Correlation of calculated inhibition values of CYP2J2 and CYP3A4. Antagonists located in the upper left quadrant are selective for CYP2J2. Luminogenic CYP2J2 assays were conducted according to the manufacturer's protocol (https://www.promega.de/resources/pubhub/enotes/cytochrome-p450-2j2-enzyme-assay-using-a-novel-bioluminescent-probe-substrate/). In order to test selectivity of a candidate CY2J2 antagonist, additional luminogenic CYP assays specific for CYP3A4 were employed and the inhibitory activity of a candidate CYP2J2 antagonists was compared to the inhibitory activity of the same antagonist against CYP3A4.

SEQ ID NO: 1 to 14: Primer Sequences

EXAMPLES

Materials and Methods

Animals

All animal experiments were performed according to the recommendations in the Guide for the Care and Use of Laboratory Animals of the National Institutes of Health and approved by the local Ethics Committees for Animal Research (Darmstadt) with the permit number F95/42. For all behavioral experiments the inventor's used only 6-12 weeks old male C57BL/6N mice purchased from commercial breeding companies (Charles River, Sulzfeld, Germany, Janvier, Le Geneset-Saint-Isle, FR). To compare mechanical thresholds the inventor's used age and sex matched littermates as control.

Prostanoid-receptor deficient mice (DP1−/−, IP−/−, EP2−/− and EP4−/−) were bred in the Institute of Clinical Pharmocology, Frankfurt, as described previously.

Paclitaxel Model of Chemotherapy-Induced Neuropathic Pain

Paclitaxel was solved in Cremophor EL/Ethanol 1:1 and diluted in saline. The dose for intraperitoneal injection was set to 6 mg/kg as described previously.

Behavioral Tests

For the determination of mechanical allodynia or thermal hypersensitivity, mice were kept in test cages on an elevated grid for at least 2 h to allow accommodation. Baseline measurements were performed using a Dynamic Plantar Aesthesiometer or a Hargreaves Apparatus (Ugo Basile, Comerio, VA, Italy) detecting withdrawal latency of the hind paws after mechanical stimulation. For the assessment of the mechanical thresholds, the steel rod was pushed against the mid-plantar hind paw with linear ascending force (0-5 g over 10 seconds, increasing 0.5 g/s) until a fast withdrawal response occurred. Slow movements of the paw were not counted. Paw withdrawal latencies (PWL) were determined in seconds (s) ±0.1 with a cut-off time of 20 s. The non-injected and injected paws were measured alternately in intervals of 5-10 min. For determination of thermal thresholds, mice were kept in test cages on a warmed glass plate (32° C.) for at least 2 h on the first day to allow accommodation. Then, the mid-plantar region of the paws was stimulated with a radiant heat device, consisting of a high intensity projector lamp, until withdrawal occurred. The non-injected and injected paws were measured alternately in intervals of 5-10 min. For all behavioral tests the investigator was blinded for treatment or genotype of the mice.

Treatments: For peripheral injections, 20 μl of 9,10-EpOME [5 μM] (Cayman, Ann Arbor, MI, USA) were injected subcutaneously (s.c.) in the mid-plantar area of the hind paw. Control animals received the corresponding volumes of DMSO (Sigma, Deisenhofen, Germany; 1.6% (v/v) in Saline). For intrathecal injections, 5 μl of 9,10-EpOME [10 μM] in 3.2% DMSO/saline (v/v) were injected by direct lumbar puncture in awake, conscious mice as described previously. Terfenadine or Loratadine (both from Tocris, Bristol, UK) were injected intravenously in the tail vein.

Primary Dorsal Root Ganglia (DRG) Cultures

Murine DRGs were dissected from spinal segments and directly transferred to ice cold HBSS with CaCl2 and MgCl2 (Invitrogen, Carsbad, CA, USA). Next, isolated DRGs were incubated with collagenase/dispase (500 U/ml Collagenase; 2.5 U/ml Dispase) in neurobasal medium containing L-glutamine [2 mM] penicillin (100 U/ml), streptomycin (100 μg/ml), B-27 and gentamicin (50 μg/ml) (all from Invitrogen, Carlsbad, CA, USA) at 37° C. for 75 min. After removal of the collagenase/dispase-solution, cells were washed twice with neurobasal medium containing 10% FCS and incubated for 10 min with 0.05% trypsin (Invitrogen, Carlsbad, CA, USA). The washing steps were repeated and the cells were mechanically dissociated with a 1 ml Gilson pipette. Finally, the neurons were plated on poly-1-lysine (Sigma, Deisenhofen, Germany) coated glass cover slips and incubated with neurobasal medium containing L-glutamine [2 mM] penicillin (100 U/ml), streptomycin (100 μg/ml), B-27 and gentamicin (50 μg/ml) over night until assessment by calcium imaging.

Calcium Imaging Experiments

Calcium-Imaging experiments were performed with two different setups. First, the inventor's used an Axioscope 2 upright microscope (Zeiss, Jena, Germany) with a 10× Achroplan water immersion objective (Zeiss). The microscope was equipped with an Imago CCD camera and a Polychrome IV monochromator (all TILL Photonics, Gräfelfing, Germany). Images were acquired every 2 seconds at both wavelengths (340 nm and 380 nm) and processed using the Tillvision software 23. Later, a Leica Calcium-imaging setup was used, consisting of a Leica DMI 4000 b inverted microscope equipped with a DFC360 FX (CCD-) camera, Fura-2 filters and an N-Plan 10×/0.25 Ph1 objective (all from Leica Microsystems, Wetzlar, Germany). Images were taken every 2 seconds and processed with the LAS AF-software. For each experiment the inventor's chose an area with large cell numbers and monitored 40-110 cells simultaneously. Calcium-Imaging experiments were performed using DRG-neurons 24-48 hours after preparation. Cells were loaded with 5 μM fura-2-AM-ester and 0.02% Pluronic F-127 (both Biotium, Hayward, CA and incubated for 30 to 60 min. at 37° C. Then, the cells were washed with external solution (containing in mM: NaCl [145], CaCl2 [1.25], MgCl2 [1], KCl [5], D-glucose [10], HEPES [10]; adjusted to pH 7.3). Baseline measurements were performed in external solution at a flow rate of 1-2 ml/min. Calcium free solutions were generated by removal of CaCl2 and addition of EGTA [2 mM] and osmotically controlled by increasing NaCl concentrations to 150 mM. Stock solutions of HC-030031 (Sigma, Deisenhofen, Germany), AMG 9810, H89-dihydrochloride, 8-bromo-cAMP, GF 109203X (all from Tocris, Bristol, UK) and NGF (Merck Millipore, Darmstadt, GE) were diluted in external solution to their final concentrations.

Quantitative Real-Time PCR

Lumbal DRGs were dissected from mice at indicated time points and RNA was extracted using the mirVana™ miRNA Isolation Kit (Ambion, life technologies, Carlsbad, CA, USA). Reverse transcription and Real-time PCR were prefomed using the TaqMan® system (life technologies, Carlsbad, CA, USA) and evaluated with the ΔΔC(T)-method as described previously 24,25. The following oligonucleotides were used for amplification of cDNA:

TABLE 1

Primer sequences used for quantitative real-time PCR from murine tissue, a = MGH primer bank, ID: 160948617c2.

| Gene | Forward | Reverse |
|---|---|---|
| CYP2C29 | 5'GCCTCAAAGCCTACTGTCA-3' (SEQ ID NO 1) | 5'- AACGCCAAAACCTTTAATC-3'(SEQ ID NO 2) |
| CYP2C37 | 5'-ATACTCTATATTTGGGCAGG-3'(SEQ ID NO 3) | 5'- GTTCCTCCACAAGGCAAC-3'(SEQ ID NO 4) |
| CYP2C38 | 5'-TTGCCTTCTGTAATCCCCC-3'(SEQ ID NO 5) | 5'-TCTAACGCAGGAATGGATAAAC-3'(SEQ ID NO 6) |
| CYP2C39 | 5'-GGAGACAGAGCTGTGGC-3'(SEQ ID NO 7) | 5'-TAAAAACAATGCCAAGGCCG-3'(SEQ ID NO 8) |
| CYP2C44 | 5'-CTTTCCAACGAGCGATTCCC-3'(SEQ ID NO 9) | 5'-TGTTTCTCCTCCTCGATCTTGC-3'(SEQ ID NO 10) |
| CYP2J6 | 5'-GGCCTCCCACCTAGTGGAA-3'(SEQ ID NO 11) | 5'-ATAACCTCGTCCAGTAACCTCA-3'(SEQ ID NO 12) |
| CYP3A11 | 5'-GACAAACAAGCAGGGATGGAC-3'(SEQ ID NO 13) | 5'- CCAAGCTGATTGCTAGGAGCA-3'(SEQ ID NO 14) |

Determination of EETs by Liquid Chromatography-Tandem Mass Spectrometry (LC-MS/MS)

Sample extraction and standards: Sample extraction was performed as described previously. Briefly, stock solutions with 2500 ng/ml of all analytes were prepared in methanol. Working standards were obtained by further dilution with a concentration range of 0.1-250 ng/ml for EETs, EpOMEs and DiHOMEs and HODEs Sample extraction was performed with liquid-liquid-extraction. Therefore tissue or cell culture medium was extracted twice with 600 µl ethyl acetate. The combined organic phases were removed at a temperature of 45° C. under a gentle stream of nitrogen. The residues were reconstituted with 50 µl of methanol/water/ (50:50, v/v), centrifuged for 2 min at 10,000×g and then transferred to glass vials (Macherey-Nagel, Düren, Germany) prior to injection into the LC-MS/MS system.

Instrumentation for measuring epoxylipids and HODEs: The LC-MS/MS system consisted of an API 4000 triple quadrupole mass spectrometer (Applied Biosystems, Darmstadt, Germany), equipped with a Turbo-V-source operating in negative ESI mode, an Agilent 1100 binary HPLC pump and degasser (Agilent, Waldbronn, Germany) and an HTC Pal autosampler (Chromtech, Idstein, Germany) fitted with a 25 µL LEAP syringe (Axel Semrau GmbH, Sprockhövel, Germany). High purity nitrogen for the mass spectrometer was produced by a NGM 22-LC-MS nitrogen generator (cmc Instruments, Eschborn, Germany). For the chromatographic separation a Gemini NX C18 column and precolumn were used (150 mm×2 mm i. d., 5 µm particle size and 110 Å pore size from Phenomenex, Aschaffenburg, Germany). A linear gradient was employed at a flow rate of 0.5 ml/min mobile phase with a total run time of 17.5 minutes. Mobile phase A was water/ammonia (100:0.05, v/v) and B acetonitrile/ammonia (100:0.05, v/v). The gradient started from 85% A to 10% within 12 min. This was held for 1 min at 10% A. Within 0.5 min the mobile phase shifted back to 85% A and was held for 3.5 min to equilibrate the column for the next sample. The injection volume of samples was 20 µl. Quantification was performed with Analyst Software V 1.4.2 (Applied Biosystems, Darmstadt, Germany) employing the internal standard method (isotope-dilution mass spectrometry). Ratios of analyte peak area and internal standard area (y-axis) were plotted against concentration (x-axis) and calibration curves were calculated by least square regression with 1/concentration2 weighting.

[35S] GTPγS Binding Assays

To measure activation of a putative of a G-protein coupled receptor, GTPγS binding assays were performed with membrane preparations of DRGs from adults rats using 1 µM 9,10-EpOME (Cayman, Ann Arbor, MI, USA) and fresh [35S] GTPγS (1250 Ci/mmol, Perkin Elmer, Waltham, MA, USA).

Measurement of iCGRP

CGRP-measurements were performed as described previously 32 using a CGRP-enzyme immune assay kit (SpiBio, Bertin pharma, France). For CGRP-measurements from DRG cultures, DRGs of wild type BL/6N mice were dissected and treated as described above and cultured overnight in 48 well plates.

Data Analysis and Statistics

All data are presented as mean ±s.e.m. To determine statistically significant differences in all behavioral experiments analysis of variance (ANOVA) for repeated measures was used followed by post hoc Bonferroni correction using GraphPad Prism. For in vitro experiments comparing only two groups, student's t-test was carried out. $P<0.05$ was considered as statistically significant.

Cytochrome P450 Luciferase Assays

CYP2J2 and CYP3A4 Glo assays were performed according to manufacturers instructions (P450-Glo™, Promega).
Protocol of the CYP2J2 assay:
Preparation of the CYP2J2-enzyme (2 nM)/Luciferin-2J2/ 4F12 substrate (2 µM) mix 5 µl/well using MultiDrop,
Addition 50 nl/well of compounds (10 µM end concentration)/DMSO(0.5% end concentration) using Echo
Incubation for 30 min at 37° C.
Addition of NADPH regeneration solution 5 µl/well using MultiDrop
Incubation for 30 min at 37° C.
Addition of LDR-esterase solution 10 µl/well using MultiDrop
Incubation for 30 min at 37° C., Luminescence readout on EnSpire.

Protocol of the CYP3A4-assay:
Preparation of the CYP3A4-enzyme (2 nM)/Luciferin-IPA substrate (7 μM) mix 5 μl/well using MultiDrop,
Addition 50 μl/well of compounds (10 μM end concentration)/DMSO (0.5% end concentration) using Echo,
Incubation for 30 min at 37° C.,
Addition of NADPH regeneration solution 5 μl/well using MultiDrop,
Incubation for 30 min at 37° C.,
Addition of LDR-esterase solution 10 μl/well using MultiDrop,
Incubation for 30 min at 37° C. and Luminescence readout on EnSpire.

Example 1: CYP-Derived Lipids in Chemotherapy Induced Neuropathic Pain

To investigate, whether or not CYP-derived lipids may play a role in chemotherapy-induced neuropathic pain, the inventors injected paclitaxel or vehicle in wild type BL/6N mice and dissected the sciatic nerves, DRGs and the spinal dorsal horn 24 h post injection. Lipid concentrations were determined using LC-MS/MS. It was found that the concentrations of the oxidized linoleic acid metabolite 9,10-EpOME (FIG. 1A) but not of its sister lipid 12,13-EpOME (FIG. 1B) or their dihydro-metabolites 9,10- and 12,13-DiHOME (see Supplementary FIG. 1) is strongly elevated in DRGs respectively (FIG. 1A). Also quantified was the levels of 9- and 13-HODE (FIG. 1C, 1D), which are generated during inflammatory pain and are endogenous activators of TRPV1 33. However, the inventors could not detect any difference in their levels following paclitaxel treatment. To investigate whether the increased 9,10-EpOME-concentration in DRGs is specific for paclitaxel treatment, zymosan was injected in the hind paw of wild type BL/6N mice in order to induce inflammatory pain. The L4-L6-DRGs and the corresponding section of the dorsal horn were dissected 24 h post injection at the peak of inflammation. Lipid quantification by LC-MS/MS did not reveal any difference in 9,10-EpOME levels during inflammatory pain (FIG. 1E).

Next, the inventors characterized 9,10-EpOME concerning its effects on DRG-neurons in calcium imaging experiments. The inventors observed, that a short stimulation of 30 s with 10 μM 9,10-EpOME caused a calcium transient in DRG neurons (FIG. 2A). The inventors performed dose response analysis to investigate the potency of 9,10-EpOME in evoking calcium transients and found a maximum of 10.3% of DRG neurons responding to 25 μM of 9,10-EpOME with no significant increase in the percentage of responding neurons to higher concentrations (FIG. 2B). To analyze, whether the 9,10-EpOME evoked calcium transients result from release of intracellular calcium stores of from influx of extracellular calcium, the inventors used calcium-free external solution, containing 2 mM EGTA and stimulated DRG neurons twice with 10 μM 9,10-EpOME for 30 s. Two minutes before the second stimulation, calcium-free external solution was washed in and the neurons did not respond to 9,10-EpOME any more, thus indicating influx of external calcium caused by 9,10-EpOME (FIGS. 2C, 2D). The positive control for neurons was a final stimulation with 50 mM KCl for 30 s.

To identify the involved ion channel, selective antagonists of TRPV1 (AMG 9810, 1 μM) and TRPA1 (HC-030031, 20 μM) were used in order to block the calcium flux caused by 9,10-EpOME. DRG neurons were stimulated twice with 9,10-EpOME (10 μM, 30 s) and the cells were pre-incubated with the TRP channel antagonists for two minutes prior to the second 9,10-EpOME stimulus. The inventors observed, that the selective TRPV1 antagonist AMG 9810, but not the TRPA1 antagonist HC-030031 could block the second 9,10-EpOME-evoked calcium transient, indicating TRPV1 as targeted channel by 9,10-EpOME (FIGS. 2E, 2F).

Example 2: 9,10-EpOME Sensitizes TRPV1

Next, the inventors analyzed if 9,10-EpOME was also capable of sensitizing TRPV1 or TRPA1 in a lower and more physiological concentration (1 μM). The inventors therefore stimulated DRG neurons twice with capsaicin (200 nM, 15 s) and incubated the cells for two minutes with 9,10-EpOME [1 μM] or vehicle prior to the second capsaicin stimulus and observed a significantly stronger response of DRG neurons to capsaicin that were incubated with 9,10-EpOME, thus indicating sensitization of TRPV1 by 9,10-EpOME (FIG. 3A). To investigate the potency of 9,10-EpOME dependent TRPV1 sensitization, dose response analysis was performed using 9,10-EpOME concentrations from 250 nM to 2 μM. It was observed that a dose dependent increase in the amplitudes of the second capsaicin responses compared to vehicle. This effect seems to be specific for TRPV1, because mustard oil-dependent TRPA1-responses could not be sensitized by 9,10-EPOME [1 μM] (FIG. 2B).

To confirm the effect of TRPV1 sensitization by 9,10-EpOME with electrophysiological means, the inventors measured sEPSCs from lamina II neurons of spinal cord slices using two capsaicin stimulations [1 μM] and incubating the cells prior to the second capsaicin stimulus with 9,10-EpOME [1 μM] (FIG. 3C). Treatment of 9,10-EpOME alone slightly increased the frequency of sEPSCs. In combination with capsaicin, however, the sEPSC frequency was strongly potentiated (FIG. 3D). However, no difference in the amplitude of sEPSCs could be observed with either 9,10-EpOME, TRPV1 or the combination of both substances (FIG. 3E).

Since it is known that lipid mediated TRPV1-sensitization mostly involves activation of a G-protein coupled receptor, the inventor's performed GTPγS assays to analyze whether 9,10-EpOME is capable of activating a GPCR in DRGs and observed a significantly increased signal of GTPγS after incubation with 1 μM 9,10-EpOME (FIG. 4A). To identify the mechanism of 9,10-EpOME mediated TRPV1 sensitization, the inventor's next measured cAMP in neuron enriched DRG cultures that were stimulated with either vehicle, 9,10-EpOME, the IP-receptor agonist cicaprost or forskolin [1 μM each] for 15 minutes. Interestingly, the inventor's observed that 9,10-EpOME caused a significant increase in cAMP concentrations compared to its vehicle (FIG. 4B). These results indicate activation of a Galphas coupled receptor by 9,10-EpOME.

Since TRPV1 can be phosphorylated by PKA and PKC, both resulting in increased activity and sensitization of the channel 35, the inventors investigated whether inhibitors of PKA or PKC can reduce 9,10-EpOME-evoked TRPV1-sensitization in calcium-imaging experiments with cultured DRG neurons from wild type BL/6N mice. The inventors could reproduce the capsaicin-dependent TRPV1 sensitization using the same protocol as mentioned above with double capsaicin stimulation and an in-between incubation with 9,10-EpOME. However, the inventors observed that pre-incubation with a PKA-inhibitor (H89 dihydrochloride, 10 μM for 1 h) caused a significant reduction of 9,10-EpOME-evoked TRPV1 sensitization. (FIGS. 4C, 4D). The use of the PKC-inhibitor GF 109203X (GFX) under the same conditions (10 μM, preincubation for 1 h) did not have any effect on 9,10-EpOME derived TRPV1 sensitization (FIGS. 4E, 4F), thus pointing toward PKA- but not PKC-mediated TRPV1 sensitization by 9,10-EPOME.

The inventors then tested the Galphas-coupled prostanoid receptors for their potential involvement in 9,10-EpOME dependent TRPV1 sensitization in calcium imaging experiments. Prostanoid receptors have varying specificity for their ligand prostanoids and may as well be activated by other lipids. However, the inventors could not observe any reduction in 9,10-EpOME evoked TRPV1-sensitization in the DRGs of either Prostaglandin E receptors EP2 and EP4 or prostaglandin D- or I-receptor (DP- and IP-receptor) deficient mice (not shown). To characterize in vivo effects of 9,10-EpOME, the inventors injected the lipid in hind paws of wild type BL/6N mice and measured the thermal (FIG. 5A) and mechanical thresholds (FIG. 5B) up to 5 h post injection. In both cases, 9,10-EpOME caused a significant reduction of the pain thresholds lasting 1 h (thermal) or 2 h (mechanical) after injection (FIG. 1A, 1B). The inventors then injected 9,10-EpOME intrathecally and measured thermal and mechanical thresholds in short time intervals. A significant but rather weak reduction of the thermal thresholds 30 minutes after i.th. injection was observed (FIG. 5C). However, the mechanical thresholds were decreased for up to 1.5 h after i.th. injection of 9,10-EpOME (FIG. 5D).

Since increased activity of TRPV1 causes increased release of calcitonin gene related peptide (CGRP) promoting neurogenic inflammation 37, the inventors analyzed whether 9,10-EpOME is capable of increasing TRPV1 dependent CGRP release. The inventors dissected sciatic nerves from wild type BL/6N mice and incubated them with 9,10-EpOME alone [1 µM], or together with capsaicin [500 nM] and observed a strong increase of CGRP release with co-stimulation of capsaicin and 9,10-EpOME. The CGRP-release was significantly greater than using only capsaicin or 9,10-EpOME (FIG. 6A). To investigate if this effect is also visible in the cell somata, neuron enriched DRG-cultures with either 9,10-EpOME, capsaicin, or both substances were stimulated using two different EpOME-concentrations [1 and 2.5 µM]. Again, the release of iCGRP was significantly increased using both EpOME and capsaicin than with either of the substances. However, there was no significant increase in CGRP-release using 2.5 µM of 9,10-EPOME (FIG. 6B).

Example 3: CYP2J2 Regulates 9,10-EpOME

Next it was investigated how 9,10-EpOME synthesis is regulated during paclitaxel CIPNP. Since 9,10-EpOME is supposed to be synthesized by CYP-epoxygenases of the subfamilies 2C and 2J 16,38, the inventors examined the expression of murine CYP-expoxygenases of these subfamilies. Eight days after paclitaxel treatment, the inventors observed a stable plateau in the mechanical thresholds of paclitaxel treated mice (FIG. 7A).

The inventors then dissected DRGs of vehicle and paclitaxel treated mice and investigated the expression of murine CYP2C29, CYP2C37, CYP2C38, CYP2C39, CYP2C44, CYP2J6 and CYP3A11. However, CYP isoforms 2C29 and 2C44 could not be detected in murine DRGs. The inventors observed that CYP2J6 showed the strongest expression in the DRGs of paclitaxel treated mice compared to vehicle treatment (FIG. 7B). This increased expression in CYP2J6 correlates with increased levels of 9,10-EpOME eight days after paclitaxel treatment, as analyzed by LC-MS/MS measurement of sciatic nerve, lumbar DRGs and the spinal cord.

Example 4: CYP2J2 Antagonists Inhibit 9,10-EpOME Synthesis and Reduce CIPNP

Terfenadine, a potent inhibitor of the human CYP2J2, which is the analogue protein of murine CYP2J6, was used as an antagonist. Since the interaction sites of Terfenadone and the human CYP2J2 have already been described, the inventors aligned the amino acids of the murine CYP2J6 and the human CYP2J2 and found all putative interaction sites with Terfenadone (Leu83, Met116, Ile127, Phe30, Thr315, Ile376, Leu378, Val380, Leu402 and Thr488) at the same position in both proteins except Arg117 which is exchanged to glutamine. Based on the surprising amino acid sequence similarity between CYP2J2 and CYP2J6 Terfenadine interacts as well with CYP2J6 and inhibits the protein. To investigate the effects of Terfenadine on lipid levels, the inventors injected mice that had received paclitaxel eight days before with 1 mg·kg-1 Terfenadine i.v. After two hours, the inventors dissected the sciatic nerve, DRGs and the dorsal spinal cord and quantified epoxylipids in these tissues. The inventors could observe a significant reduction of the 9,10-EpOME concentrations in all investigated tissues (FIG. 8A). The inventors also observed, that the remaining concentrations of all measured epoxylipids and their (9,10-EpOME, 12,13-EpOME, 9,10-DiHOME, 12,13-DiHOME and 14,15-EET) were reduced significantly in DRGs, the spinal dorsal horn and the plasma, but not in the sciatic nerve of Terfenadine treated animals respectively (FIG. 8B).

The inventors next investigated whether treatment with Terfenadine may reduce Paclitaxel-induced CIPNP in mice. Therefore, the inventor's injected Terfenadine (1 or 2 mg·kg-1 or vehicle (DMSO) intravenously in mice that had already received paclitaxel eight days before.

The inventors measured the mechanical thresholds of mice 1, 2, 4 and 5 h post Terfenadine injection and could observe a significant increase in mechanical thresholds of mice that were treated with Terfenadine, lasting for 2 h. However, no significant differences between the two doses could be observed (FIG. 8C). Since Terfenadine is a histamine-1-receptor antagonist, the inventors used Loratadine, another H1-receptor-antagonist that does not inhibit CYP2J2, to investigate, if the antinociceptive effects are really caused by inhibition of CYP2J2, or the histamine-1-receptor. However, treatment with Loratadine did not reduce paclitaxel-induced CIPNP compared to the vehicle (FIG. 8D).

Example 5: Screening of New Selective CYP2J2-Antagonists

The Screens-Well® FDA Approved Drug Library v2 was screened for new selective antagonists of CYP2J2 for use in the context of the herein described invention. The enzymatic CYP-Glo luciferase based reaction was used to assay the activity of CYP2J2 and as unselective control CYP3A4. Tefenadine was used as positive control in the experiments. The Results from both screens are depicted in FIG. 9. Antagonists that showed over 60% inhibition against CYP2J2 and about 0% inhibition of CYP3A4 are regarded as selective CYP2J2 antagonists and are useful for the methods and uses as described herein, and are listed in table 2 below:

TABLE 2

| Compound ID | Average inhibition CYP2J2 (%) | Average inhibition CYP3A4 (%) | Name |
|---|---|---|---|
| c054 | 84.4 | 12.1 | Estradiol |
| c089 | 75.0 | 17.9 | Phenoxybenzamine•HCl |
| c124 | 80.8 | −23.5 | Loratadine |
| c146 | 78.2 | −4.3 | Clobetasol Propionate |
| c244 | 73.7 | −43.3 | Doxazosin Mesylate |
| c246 | 78.0 | −26.2 | Fenofibrate |
| c314 | 64.0 | 5.1 | Levonorgestrel |
| c337 | 92.8 | 15.5 | Aripiprazole |
| c440 | 76.8 | −18.5 | Halcinonide |
| c485 | 89.5 | 7.6 | Telmisartan |
| c516 | 79.1 | −82.9 | Clofazimine |
| c542 | 87.6 | 12.9 | Levothyroxine•Na |
| c595 | 81.8 | 14.0 | Alosetron•HCl |
| c596 | 75.9 | 10.7 | Fluocinonide |
| c606 | 93.6 | −6.8 | Liothyronine•Na |
| c608 | 71.5 | 17.4 | Meclizine Dihydrochloride |

Discussion 9,10-EpOME is capable of sensitizing TRPV1 in DRG neurons via a cAMP-PKA dependent mechanism in submicromolar concentrations, leading to subsequent release of iCGRP from DRGs. Other oxidized linoleic acid metabolites (OLAMs), such as 9 and 13-HODE, which are produced during excessive heating of skin, have already been shown to be direct TRPV1 agonists and to contribute to inflammatory hyperalgesia. The inventors could also detect 9- and 13-HODE in murine tissue, most predominantly in peripheral tissues.

The inventors used the CYP2J2-inhibitor Terfenadine to reduce synthesis of 9,10-EpOME and could reduce the levels of epoxylipids to about 50%. Treatment with Terfenadine resulted in reduced mechanical hypersensitivity in mice during paclitaxel CIPNP. Antagonists of CYP2J2 and its homologs are therefore useful for treating or preventing CIPNP, which was confirmed because animals that were treated with Loratadine, a selective H1-receptor antagonist, that does not affect CYP2J2, did not show an improvement in paclitaxel CIPNP, thus indicating that the effect that was observed with Terfenadine is due to inhibition of CYP2J2 and not of the histamine 1-receptor.

Chemotherapy-induced neuropathic pain and subsequent sensory dysfunctions still remain the most severe side effects of cytostatics. Especially during paclitaxel-treatment, an early acute pain syndrome can be observed which seems to be mediated by sensitization of nociceptive neurons. However, there is no information available on endogenous mediators that may contribute to this pathophysiological state. According to the inventor's data, 9,10-EpOME-dependent TRPV1 sensitization and increased activity of nociceptive neurons may thus contribute to paclitaxel acute pain syndrome (P-APS).

Currently, there is a strong unmet medical need for CIPNP therapeutics. Treatment of patients with antioxidants or neuroprotextive substances, such as amifostine or glutathione failed to ameliorate CIPNP in large randomized and placebo controlled clinical trials, and a recent Cochrane review concludes, that there is currently no evidence for functional CIPNP therapy with these substances. Moreover, antioxidants may interfere with the antineoplastic effects of cytostatics. Recently, it was reported that treatment with N-acetyl cysteine (NAC) and vitamin E increased lung tumor cell proliferation and tumor growth in mice by reducing DNA damage. In this regard, CYP2J2-inhibitors may be superior over using antioxidants, because they have been reported to even reduce cancer growth in vitro and in vivo by activating caspase-3, Bax and Bcl-2 and by reducing tumor cell migration and adherence.

The invention claimed is:

1. A method for treating chemotherapy induced peripheral neuropathic pain (CIPNP) in a subject in need of the treatment, the method comprising:

administering to the subject a therapeutically effective amount of a cytochrome P450 epoxygenase 2J2 (CYP2J2) antagonist to treat the CIPNP, the CYP2J2 antagonist selected from the group consisting of estradiol, clobetasol propionate, doxazosin mesylate, fenofibrate, levonorgestrel, aripiprazole, halcinonide, telmisartan, levothyroxine-Na, alosetron-HCl, fluocinonide, and liothyronine-Na.

2. The method according to claim 1, wherein the CYP2J2-antagonist is telmisartan.

3. The method according to claim 1, comprising administering the therapeutically effective amount of the cytochrome P450 epoxygenase 2J2 (CYP2J2) antagonist to the subject prior to, during, or after a chemotherapy treatment on the subject.

4. The method according to claim 3, wherein the chemotherapy comprises the administration of a chemotherapeutic agent to the subject, and wherein the chemotherapeutic agent is selected from the group consisting of a Cytarabine and Five Fluorouracil, a platin agent and a taxane.

5. The method according to claim 3, wherein the chemotherapy comprises the administration of a chemotherapeutic agent to the subject, and wherein the chemotherapeutic agent is paclitaxel, docetaxel or cabazitaxel.

6. The method according to claim 3, comprising administering the therapeutically effective amount of the cytochrome P450 epoxygenase 2J2 (CYP2J2) antagonist to the subject before the chemotherapy treatment on the subject.

* * * * *

SEQUENCE LISTING

<160> NUMBER OF SEQ ID NOS: 14

<210> SEQ ID NO 1
<211> LENGTH: 19
<212> TYPE: DNA
<213> ORGANISM: Artificial
<220> FEATURE:
<223> OTHER INFORMATION: Primer sequence

<400> SEQUENCE: 1
gcctcaaagc ctactgtca                                                  19

<210> SEQ ID NO 2
<211> LENGTH: 19
<212> TYPE: DNA
<213> ORGANISM: artificial
<220> FEATURE:
<223> OTHER INFORMATION: Primer sequence

<400> SEQUENCE: 2
aacgccaaaa cctttaatc                                                  19

<210> SEQ ID NO 3
<211> LENGTH: 20
<212> TYPE: DNA
<213> ORGANISM: artificial
<220> FEATURE:
<223> OTHER INFORMATION: Primer sequence

<400> SEQUENCE: 3
atactctata tttgggcagg                                               20

<210> SEQ ID NO 4
<211> LENGTH: 18
<212> TYPE: DNA
<213> ORGANISM: artificial
<220> FEATURE:
<223> OTHER INFORMATION: Primer sequence

<400> SEQUENCE: 4
gttcctccac aaggcaac                                                 18

<210> SEQ ID NO 5
<211> LENGTH: 19
<212> TYPE: DNA
<213> ORGANISM: artificial
<220> FEATURE:
<223> OTHER INFORMATION: Primer sequence

<400> SEQUENCE: 5
ttgccttctg taatccccc                                                19

<210> SEQ ID NO 6
<211> LENGTH: 22
<212> TYPE: DNA
<213> ORGANISM: artificial
<220> FEATURE:
<223> OTHER INFORMATION: Primer sequence

<400> SEQUENCE: 6
tctaacgcag gaatggataa ac                                            22

<210> SEQ ID NO 7
<211> LENGTH: 17
<212> TYPE: DNA
<213> ORGANISM: artificial
<220> FEATURE:
<223> OTHER INFORMATION: Primer sequence

<400> SEQUENCE: 7
ggagacagag ctgtggc                                                  17

<210> SEQ ID NO 8
<211> LENGTH: 20
<212> TYPE: DNA
<213> ORGANISM: artificial
<220> FEATURE:
<223> OTHER INFORMATION: Primer sequence

<400> SEQUENCE: 8
taaaaacaat gccaaggccg                                               20

<210> SEQ ID NO 9
<211> LENGTH: 20
<212> TYPE: DNA
<213> ORGANISM: artificial
<220> FEATURE:
<223> OTHER INFORMATION: Primer sequence

<400> SEQUENCE: 9
ctttccaacg agcgattccc                                               20

<210> SEQ ID NO 10
<211> LENGTH: 22

```
<212> TYPE: DNA
<213> ORGANISM: artificial
<220> FEATURE:
<223> OTHER INFORMATION: Primer sequence

<400> SEQUENCE: 10
tgtttctcct cctcgatctt gc                                              22

<210> SEQ ID NO 11
<211> LENGTH: 19
<212> TYPE: DNA
<213> ORGANISM: artificial
<220> FEATURE:
<223> OTHER INFORMATION: Primer sequence

<400> SEQUENCE: 11
ggcctcccac ctagtggaa                                                  19

<210> SEQ ID NO 12
<211> LENGTH: 22
<212> TYPE: DNA
<213> ORGANISM: artificial
<220> FEATURE:
<223> OTHER INFORMATION: Primer sequence

<400> SEQUENCE: 12
ataacctcgt ccagtaacct ca                                              22

<210> SEQ ID NO 13
<211> LENGTH: 21
<212> TYPE: DNA
<213> ORGANISM: artificial
<220> FEATURE:
<223> OTHER INFORMATION: Primer sequence

<400> SEQUENCE: 13
gacaaacaag cagggatgga c                                               21

<210> SEQ ID NO 14
<211> LENGTH: 21
<212> TYPE: DNA
<213> ORGANISM: artificial
<220> FEATURE:
<223> OTHER INFORMATION: Primer sequence

<400> SEQUENCE: 14
ccaagctgat tgctaggagc a                                               21
```